(12) United States Patent
Percy et al.

(10) Patent No.: US 10,634,672 B2
(45) Date of Patent: *Apr. 28, 2020

(54) METHOD OF DETECTING A MICROORGANISM USING CHROMATOGRAPHIC ENRICHMENT

(71) Applicant: 3M INNOVATIVE PROPERTIES COMPANY, Saint Paul, MN (US)

(72) Inventors: Neil Percy, Saint Paul, MN (US); Gregory W. Sitton, Minneapolis, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 355 days.

This patent is subject to a terminal disclaimer.

(21) Appl. No.: 15/514,534

(22) PCT Filed: Oct. 5, 2015

(86) PCT No.: PCT/US2015/053943
§ 371 (c)(1),
(2) Date: Mar. 27, 2017

(87) PCT Pub. No.: WO2016/057371
PCT Pub. Date: Apr. 14, 2016

(65) Prior Publication Data
US 2017/0219577 A1    Aug. 3, 2017

Related U.S. Application Data

(60) Provisional application No. 62/060,621, filed on Oct. 7, 2014.

(51) Int. Cl.
*G01N 33/558*    (2006.01)
*G01N 33/569*    (2006.01)

(52) U.S. Cl.
CPC ..... *G01N 33/558* (2013.01); *G01N 33/56911* (2013.01); *G01N 2469/10* (2013.01)

(58) Field of Classification Search
USPC .............. 422/400, 401, 420, 425; 435/287.7, 435/287.9, 970; 436/514
See application file for complete search history.

(56) References Cited

U.S. PATENT DOCUMENTS 5,011,779 A * 4/1991 Maimon ............... B01L 3/0293
                                                       422/504
5,079,142 A    1/1992 Coleman
(Continued)

FOREIGN PATENT DOCUMENTS

EP    2 330 402    6/2011
WO    1988/08534    11/1988
(Continued)

OTHER PUBLICATIONS

Chen, J. et al.; "Automated immunomagnetic separation for the detection of *Escherichia coli* O157:H7 from spinach"; International Journal of Food Microbiology; vol. 179; 2014; pp. 33-37.
(Continued)

*Primary Examiner* — Christopher L Chin
(74) *Attorney, Agent, or Firm* — Eric E. Silverman

(57) ABSTRACT

A device is provided. The device comprises a casing comprising an interior, a first opening, and a second opening; and a porous carrier comprising a sample-receiving zone and a target cell-binding zone. The porous carrier defines a first fluid pathway that extends from the sample-receiving zone to the target cell-binding zone. At least portion of the porous carrier is disposed in the interior of the casing. A second fluid pathway comprising a central axis extends through the casing from the first opening and the second opening, the second fluid pathway intersecting the porous carrier at the target cell-binding zone. The central axis is oriented (Continued)

orthogonally with respect to the porous carrier. Methods of using the device to detect a target microorganism are also provided.

17 Claims, 8 Drawing Sheets

(56) References Cited

U.S. PATENT DOCUMENTS

| | | | |
|---|---|---|---|
| 5,772,961 A * | 6/1998 | Mico | B01L 3/5023 422/412 |
| 5,869,003 A | 2/1999 | Nason | |
| 7,241,626 B2 | 7/2007 | Li | |
| 9,784,653 B2 | 10/2017 | Xia et al. | |
| 10,281,466 B2 * | 5/2019 | Percy | G01N 33/558 |
| 2004/0101966 A1 * | 5/2004 | Davis | A01N 1/02 436/43 |
| 2004/0132211 A1 | 7/2004 | Li | |
| 2005/0129579 A1 * | 6/2005 | Morrison | B26F 1/02 422/400 |
| 2006/0040408 A1 | 2/2006 | Jones | |
| 2007/0287198 A1 | 12/2007 | LaBorde | |
| 2011/0097814 A1 | 4/2011 | Bommarito et al. | |

FOREIGN PATENT DOCUMENTS

| | | |
|---|---|---|
| WO | 2000/70327 | 11/2000 |
| WO | 2004/011942 | 2/2004 |
| WO | 2009/137059 | 11/2009 |
| WO | 2012/110693 | 8/2012 |
| WO | 2013/184397 | 12/2013 |
| WO | 2016/057374 | 4/2016 |

OTHER PUBLICATIONS

International Search Report for PCT/US2015/053943 dated Dec. 22, 2015.

Fang et al, "Lateral flow biosensor for DNA extraction-free detection of *Salmonella* based on aptamer mediated strand displacement amplification," 2014, *Biosensors and Bioelectronics*, 56:192-97.

* cited by examiner

METHOD OF DETECTING A MICROORGANISM USING CHROMATOGRAPHIC ENRICHMENT

CROSS REFERENCE TO RELATED APPLICATION

This application is a national stage filing under 35 U.S.C. 371 of PCT/US2015/053943, filed Oct. 5, 2015, which claims the benefit of U.S. Provisional Patent Application No. 62/060,621, filed Oct. 7, 2014, the disclosure of which is incorporated by reference in its entirety herein.

BACKGROUND

In some instances, the detection of particular cells (e.g., microorganisms) in a complex matrix (e.g., food, wound exudate, saliva, sputum, feces) can be difficult because the matrix contains materials (e.g., biomolecules, enzymes, chemicals, ions) that interfere with one or more component of the detection system. Therefore, it is common for operators to use various processes to reduce the inhibitory effects of the materials found in the matrix. One approach to reduce matrix effects is to dilute the matrix-containing sample to reduce the concentration of the inhibitory materials. However, this approach can limit the overall detection sensitivity of the test.

Another approach for reducing the effects of the sample matrix is to isolate and/or purify the cells of interest using immunomagnetic separation (IMS), as described by Chen et al. ("Automated immunomagnetic separation for the detection of *Escherichia coli* O157:H7 from spinach"; 2014; International Journal of Food Microbiology; 179:33-37). This approach has gained popularity because the process has been automated to eliminate steps that required operator intervention to achieve useful separation of the target cells from the matrix materials. In addition, the use of IMS processes has resulted in improved detection sensitivity.

In spite of the advancements in sample preparation, there remains a need for simple, rapid processes for preparing a sample to detect a target cell).

SUMMARY

In general, the present disclosure relates to methods and devices for detecting a target cell (e.g., a microorganism). In particular, the present disclosure relates to the use of a chromatographic device to enrich the target cells at a predetermined location within a chromatographic device and, subsequently, to release the predetermined location and/or target cells from the device. After releasing the predetermined location and/or target cells from the device, the cells can be detected and optionally identified using one or more of a variety of detection procedures known in the art. Advantageously, the methods and devices of the present disclosure enrich the target cells relative to non-target cells and other particles or molecules that may otherwise interfere with detection of the target cells. In addition, the enrichment achieved by the methods provides increased sensitivity of detection of the target cells, especially when the target cells are present in a sample at a low concentration.

In one aspect, the present disclosure provides a first method of detecting a target microorganism. The method can comprise contacting a liquid sample with a porous carrier of a sample preparation device; the device comprising a casing comprising a first and second opening and the porous carrier. The porous carrier comprises a sample-receiving zone at a first predefined location and a target cell-binding zone at a second predefined location, the porous carrier defining a first fluid pathway extending from the sample-receiving zone through the target cell-binding zone. A second fluid pathway extends through the casing from the first opening to the second opening, the second fluid pathway intersecting the porous carrier at the target cell-binding zone. The first method further can comprise allowing at least a portion of the liquid sample to move longitudinally through the porous carrier from the sample-receiving zone toward the target cell-binding zone; after the at least a portion of the liquid has moved to the target cell-binding zone, urging a detachment member through the second fluid pathway from the first opening to the second opening and thereby expelling a portion of the target cell-binding zone; and processing the portion of the target cell-binding zone, or a cell released therefrom, to detect an indication of the target microorganism.

In another aspect, the present disclosure provides a second method of detecting a target microorganism. The method can comprise contacting a liquid sample with a porous carrier of a sample preparation device; the device comprising a casing comprising a first and second opening and the porous carrier. The porous carrier comprises a sample-receiving zone at a first predefined location and a target cell-binding zone at a second predefined location, the porous carrier defining a first fluid pathway extending from the sample-receiving zone through the target cell-binding zone. A second fluid pathway extends through the casing from the first opening to the second opening, the second fluid pathway intersecting the porous carrier at the target cell-binding zone. The second method further can comprise allowing at least a portion of the liquid sample to move longitudinally through the porous carrier from the sample-receiving zone toward the target cell-binding zone; after the at least a portion of the liquid has moved to the target cell-binding zone, urging a target release solution through the second fluid pathway and thereby expelling from the device in a part of the target release solution comprising a target microorganism, if present in the second fluid pathway; and processing the part of the release solution to detect an indication of the target microorganism.

In any of the above embodiments of the first and second methods, after the at least a portion of the liquid has moved to the target cell-binding zone, the method further can comprise a step of passing a wash solvent through the porous carrier via the second fluid pathway. In any of the above embodiments of the first and second methods, the method further can comprise positioning a receptacle proximate the second opening, wherein expelling a portion of the target cell-binding zone or expelling the part of the release solution further comprises moving the portion of the target cell-binding zone or moving the part of the release solution into the receptacle.

In yet another aspect, the present disclosure provides a device. The device can comprise a casing comprising an interior, a first opening, and a second opening; and a porous carrier comprising a sample-receiving zone and a target cell-binding zone. The porous carrier defines a first fluid pathway that extends from the sample-receiving zone to the target cell-binding zone. At least portion of the porous carrier is disposed in the interior of the casing. A second fluid pathway comprising a central axis extends through the casing from the first opening and the second opening, the second fluid pathway intersecting the porous carrier at the target cell-binding zone. The central axis can be oriented orthogonal to the porous carrier.

In any of the above embodiments, the casing further can comprise a first conduit that extends along the passageway from the sample port to the interior of the casing. In any of the above embodiments, the casing further can comprise a second conduit that extends along the passageway from the first opening to the interior of the casing. In any of the above embodiments, the device further can comprise an absorbent body disposed proximate the second opening, wherein the absorbent body is spaced apart from the porous carrier. In any of the above embodiments, the device further can comprise a detachment member dimensioned to traverse the second fluid pathway from the first opening to the second opening, wherein a portion of the detachment member is slideably engaged in the second fluid pathway. In any of the above embodiments, the detachment member can comprise a cutting structure. In any of the above embodiments, the detachment member can be configured to urge an aqueous liquid through the second conduit.

In yet another aspect, the present disclosure provides a kit. The kit can comprise the device of any of the above embodiments. In any embodiment, the kit further can comprise a wash liquid. In any embodiment, the kit further can comprise a release solution.

The terms "comprises" and variations thereof do not have a limiting meaning where these terms appear in the description and claims.

As used herein, "a," "an," "the," "at least one," and "one or more" are used interchangeably. Thus, for example, a binding partner can be interpreted to mean "one or more" binding partners.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

DETAILED DESCRIPTION

Figure 1:
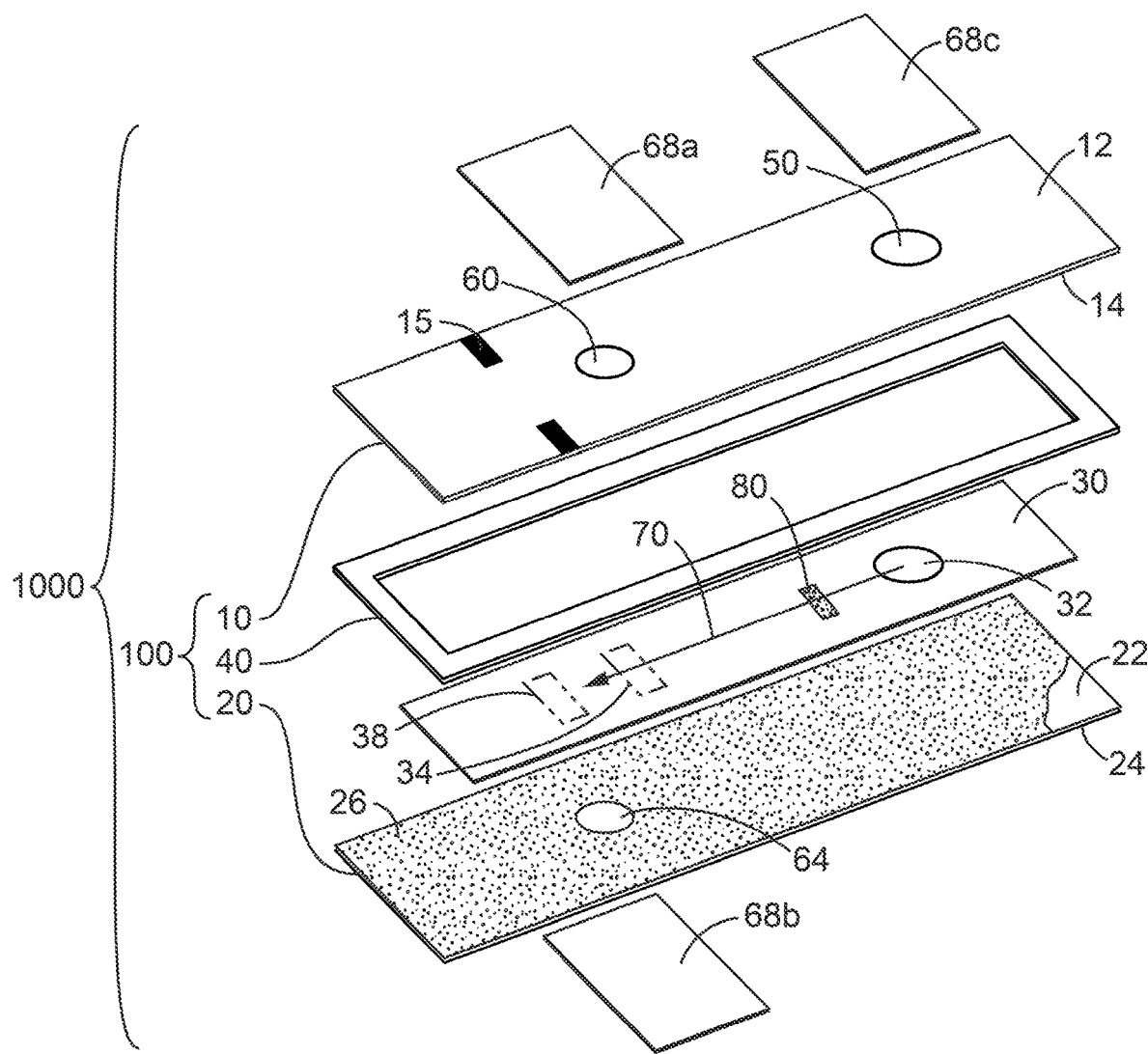
FIG. 1 is a partially exploded perspective view of one embodiment of a sample preparation device according to the present disclosure.
Figure 2:
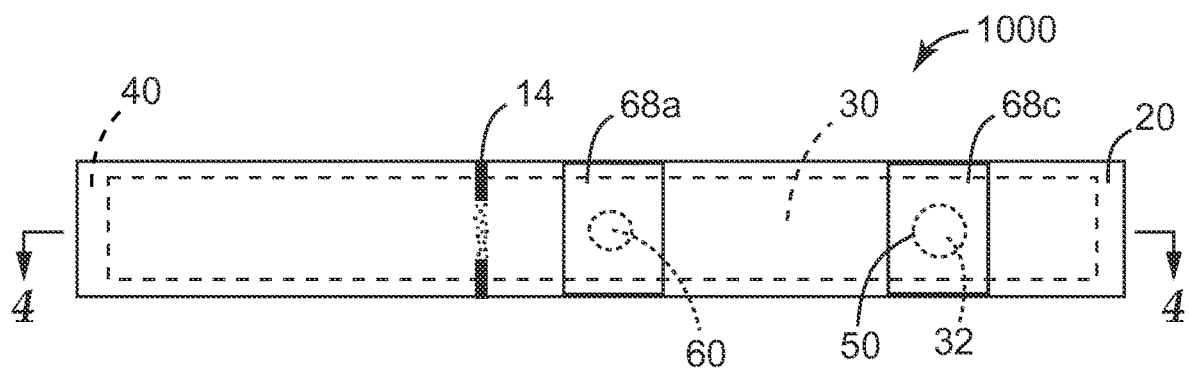
FIG. 2 is a plan view of the device of FIG. 1.
Figure 3:
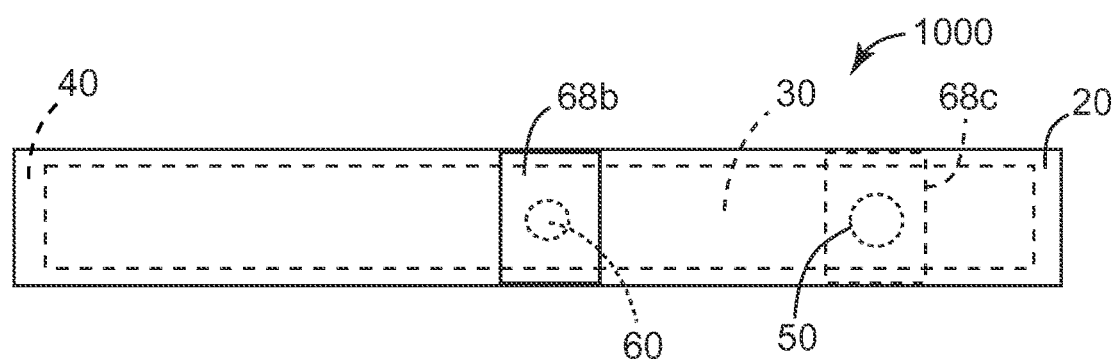
FIG. 3 is a bottom view of the device of FIG. 1.
Figure 4:
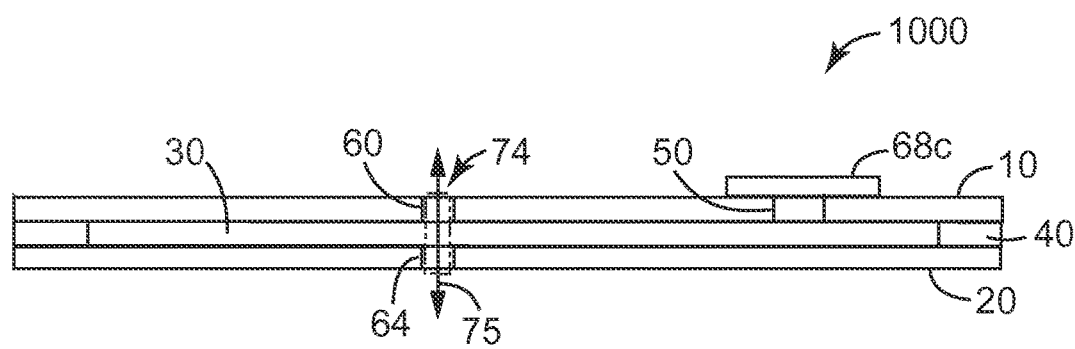
FIG. 4 is a cross-sectional side view of the device of FIG. 2, taken along line 4-4, with two of the cover elements removed in order to show a second fluid pathway extending through the casing.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the device, to indicate or imply necessary or required orientations of the device, or to specify how the invention described herein will be used, mounted, displayed, or positioned in use.

The present disclosure generally relates to methods and devices to facilitate detection of a target cell (e.g., a target microorganism or group of microorganisms). "Target cell", as used herein, refers to a particular cell (e.g., a normal cell, a cancer cell) whose presence (or absence) in a sample is to be determined. "Target microorganism", as used herein, refers to a particular microorganism whose presence (or absence) in a sample is to be determined. The target microorganism may be a pathogenic organism or it may be a nonpathogenic organism whose presence is associated with the presence of other organisms, some of which may be pathogenic. In particular, the present disclosure relates to methods employing a chromatographic device, wherein the chromatographic device is configured to facilitate removal of a target cell captured therein without having to disassemble or partially disassemble the chromatographic device. Advantageously, the methods and device of the present disclosure permit the operator to release at least one of the captured cells for further analysis. Even more advantageously, the at least one captured cell can be released easily and directly into a receptacle (e.g., a reaction tube) without unduly exposing the portion to a potential source of contamination.

One aspect of the present invention is that it may be used in a method to detect target cells present in a wide variety of sample materials. The devices and methods of the present invention may be used for a variety of applications where it is desirable to detect cells (e.g., microorganisms present in a sample material (e.g., a food sample, a soil sample, a water sample, a clinical sample). In any embodiment, the sample material may be obtained from various surfaces including, but not limited to, food surfaces (e.g. beef carcasses, exterior surfaces of produce), food processing surfaces, water or water film surfaces, patient surfaces, patient treatment surfaces, hospital environmental surfaces, clinic environmental surfaces, and forensic environmental surfaces. The samples may consist substantially of solid, semi-solid, gelatinous, or liquid material, alone or in various combinations. In any embodiment of the method of the present disclosure, the sample is suspended in a liquid (e.g., an aqueous liquid) that is capable of moving (e.g., by capillary force) through the porous carrier. The device of the present disclosure, as well as the inventive methods, may be used to determine, qualitatively or quantitatively, the presence of one or more cells of interest from the original sample.

An exemplary cell of interest to detect in a sample is *Staphylococcus aureus* ("*S. aureus*"). This is a pathogen causing a wide spectrum of infections including: superficial lesions such as small skin abscesses and wound infections; systemic and life threatening conditions such as endocarditis, pneumonia and septicemia; as well as toxinoses such as food poisoning and toxic shock syndrome. Some strains (e.g., Methicillin-Resistant *S. aureus* or MRSA) are resistant to all but a few select antibiotics.

Exemplary analytes of interest to detect in food processing areas and samples are members of the genus *Listeria*. *Listeria* are classified as gram-positive, rod-shaped bacteria and consist of the species *Listeria monocytogenes*, *L. innocua*, *L. welshimeri*, *L. seeligeri*, *L. ivanovii*, and *L. grayi*. Among these, *L. monocytogenes* is responsible for the majority of human listeriosis cases and immunocompromised, pregnant women, elderly, and newborns have increased susceptibility to infection. The most common symptoms of listeriosis are septicemia, meningitis, and miscarriages.

Other microorganisms of particular interest for analytical purposes include prokaryotic and eukaryotic organisms, particularly Gram positive bacteria, Gram negative bacteria, fungi, *mycoplasma*, and yeast. Particularly relevant organisms include members of the family Enterobacteriaceae, or the family Micrococcaceae or the genera *Staphylococcus* spp., *Streptococcus* spp., *Pseudomonas* spp., *Enterococcus* spp., *Salmonella* spp., *Legionella* spp., *Shigella* spp. *Yersinia* spp., *Enterobacter* spp., *Escherichia* spp., *Bacillus* spp., *Vibrio* spp., *Clostridium* spp., *Corynebacteria* spp. as well as, *Aspergillus* spp., *Fusarium* spp., and *Candida* spp. Particularly virulent organisms include *Staphylococcus aureus* (including resistant strains such as Methicillin Resistant *Staphylococcus aureus* (MRSA)), *S. epidermidis*, *Streptococcus pneumoniae*, *S. agalactiae*, *S. pyogenes*, *Enterococcus faecalis*, Vancomycin Resistant *Enterococcus* (VRE), Vancomycin Resistant *Staphylococcus aureus* (VRSA), Vancomycin Intermediate-resistant *Staphylococcus aureus* (VISA), *Bacillus anthracia*, *Pseudomonas aeruginosa*, *Escherichia coli*, *Aspergillus niger*, *A. fumigatus*, *A. clavatus*, *Fusarium solani*, *F. oxysporum*, *F. chlamydosporum*, *Vibrio cholera*, *V. parahemolyticus*, *Salmonella cholerasuis*, *S. typhi*, *S. typhimurium*, *Candida albicans*, *C. glabrata*, *C. krusei*, *Enterobacter sakazakii*, *Escherichia. coli* O157, ESBL-containing microorganisms, and multiple drug resistant Gram negative rods (MDR).

FIGS. 1-4 show various views of one embodiment of a sample preparation device 1000 according to the present disclosure. The sample preparation device 1000 comprises a casing 100 that encases at least a portion of a porous carrier 30. In any embodiment, the casing 100 may be hollow (i.e., it may comprise a void space in which the porous carrier 30 is disposed). Flanking at least a part of the porous carrier 30 or surrounding the entire porous carrier as shown in the illustrated embodiment of FIGS. 1 through 4, is an optional spacer 40. Although shown as a unitary part in the illustrated embodiments herein, it is contemplated the spacer may comprise a plurality of parts (not shown) that may or may not have interconnections. The spacer 40 functions to keep parts of the casing 100 spaced-apart and, thereby, creating a void space in which the porous carrier 30 is disposed.

The porous carrier 30 comprises a sample-receiving zone 32 and a target cell-binding zone 34 that is spaced apart from the sample-receiving zone. Accordingly, the porous carrier 30 defines a first fluid pathway 70 that extends from the sample-receiving zone to the target cell-binding zone. Thus, when a liquid sample (e.g., an aqueous liquid sample (not shown) contacts the porous carrier 30 (e.g., at the sample-receiving zone 32), at least a portion of the liquid in the sample moves from the sample-receiving zone to the target cell-binding zone 34. In any embodiment, the liquid moves through the porous carrier 30 for example via capillary force, gravitational force, centrifugal force, or a combination of any two or more of the foregoing forces. In any embodiment, the porous carrier 30 may be generally flat (i.e., sheet-like) and thereby define a plane.

In the illustrated embodiment of FIGS. 1 through 4, the casing 100 comprises an assembly of two separately-formed parts that include a first piece 10 that defines a first side of the casing and a second piece 20 that defines a second side opposite the first side of the casing. The first piece 10 has an external-facing first side 12 and an internal-facing second side 14. The second side 14 faces the porous carrier 30. The second piece 20 has an external-facing fourth side 24 and an internal-facing third side 22. The third side 22 faces the porous carrier 30. The casing 100 of the illustrated embodiment further comprises the optional spacer 40, which helps enclose the porous carrier 30.

In any embodiment, the first piece 10 may comprise metal, glass, or polymeric material (e.g., polyolefin, polyester, polystyrene, or combinations thereof) that is formed using processes known in the art (e.g., extruding, molding, casting, stamping). In any embodiment, the second piece 20 may comprise metal, glass, or polymeric material (e.g., polyolefin, polyester, polystyrene, or combinations thereof) that is formed using processes known in the art (e.g., extruding, molding, casting, stamping, 3D printing). In any embodiment, the first piece 10 may comprise the same material as the second piece 20 and/or different material than the second piece 20. In any embodiment, a portion of or the entire first piece 10 and a portion of or the entire second piece 20 of the casing 100 is fabricated from a material (e.g., a polymeric material) that is optically-transmissible. Thus, an optically-detectable indicator disposed on and/or in the porous carrier 30 may be optically (e.g., visually) detected by observing it through the casing 100.

Preferably, both the first piece 10 and second piece 20 comprise a water-resistant material and/or further comprise a water-resistant coating (e.g., a coating of hydrophobic adhesive, not shown) disposed on the second side 14 and third side 22, respectively. An optional hydrophobic adhesive, if present on the second side 14, can couple the first piece 10 to the spacer 40, the porous carrier 30, and/or the second piece 20. Similarly, an optional hydrophobic adhesive (adhesive layer 26), when present on the third side 22, can couple the second piece 20 to the spacer 40, the porous carrier 30, and/or the first piece 10. In any embodiment, the spacer 40 may have an optional adhesive layer (not shown) coated on either or both sides to facilitate coupling the spacer 40 to the first piece 10 and/or second piece 20.

It is contemplated that, in any embodiment, the casing of the device may be a unitary part (not shown). The unitary casing may be formed, for example, by molding a thermoplastic polymer using processes (e.g., injection molding) that are well-known in the art. The unitary casing may comprise an opening (e.g., a sealable opening) through which a portion or the entire porous carrier can be inserted into the casing.

Returning to the drawings, the casing 100 includes a sample port 50, a first opening 60 spaced apart from the sample port, and a second opening 64, opposite the first opening. The first opening 60 and the second opening 64 preferably are aligned or partially aligned such that an object can pass along a substantially straight line (not shown) that passes through both the first opening 60 and second opening 64. The first opening 60 may be the same size of a different size than the second opening 64. The sample port 50 is disposed proximate the origin of a first fluid pathway (first fluid pathway 70 described herein) that extends through the porous carrier 30 from the sample port 50 to and beyond the first opening 60.

The sample port 50 and first opening 60 optionally are disposed on the same side, and in the same piece, of the casing 100. The sample port 50 provides access to the porous carrier 30 proximate a sample-receiving zone 32 of the porous carrier. Thus, in the illustrated embodiment of FIGS. 1-4, the sample-receiving zone 32 is disposed in the interior of the casing 100. The first opening and second opening (first opening 60 and second opening 64, respectively) define the termini of a second fluid pathway that extends through the casing 100.

The second fluid pathway 74 (FIG. 4) comprises a central axis 75 and intersects the porous carrier 30 at a predetermined location (i.e., at target cell-binding zone 34, described herein). In any embodiment, the path of the second fluid pathway 74 is substantially straight. Accordingly, each of the first opening 60 and second opening 64 provides a direct access via the second fluid pathway 74 to the porous carrier 30 proximate the target cell-binding zone 34. In any embodiment of a device according to the present disclosure, the central axis 75 of the second fluid pathway 74 is oriented orthogonal to the first fluid pathway defined by the porous carrier 30.

The second fluid pathway 74 serves at least two functions: i) it provides a fluid pathway to pass a liquid (e.g., an aqueous liquid such as a buffer) through the target cell-binding zone 34 of the porous carrier, and ii) it provides an ingress (e.g., the first opening 60) through which a detachment member (described herein) can be inserted into the device 1000 and urged through the second fluid pathway 74, thereby detaching at least a portion of or, alternatively, the entire target cell-binding zone 34 of the porous carrier 30 as well as an egress (e.g., the second opening 64) through which the detached part of the target cell-binding zone can be expelled from the device. It is contemplated that, alternatively, the second opening 64 may function as the ingress and the first opening 60 may function as the egress.

In any embodiment, either one or both of the first opening 60 and second opening 64 can be shaped and dimensioned to receive a liquid-dispensing instrument (e.g., a syringe). The opening(s) further may be dimensioned to be coupled (e.g., by friction-fit) with the liquid-dispensing instrument such that the coupling is substantially sealed against liquid leaks. Advantageously, devices having this configuration facilitate passing a liquid (e.g., a buffer solution) through the target cell-binding zone 34 of the porous medium 30 using positive pressure, negative pressure, or a combination thereof.

In any embodiment, the sample preparation device 1000 optionally may further comprise one or more cover elements (e.g., first cover element 68c, second cover element 68a, and third cover element 68b, respectively) that removably cover the sample port 50, the first opening 60, and/or the second opening 64, respectively. The cover elements 68a-68c may be fabricated from a suitable material (e.g., plastic) and may be dimensioned and shaped to provide a friction fit, snap-fit, or screw-in connection to the port or opening, for example. Alternatively, in any embodiment, the cover element may be dimensioned to provide a friction fit, snap-fit, or screw-in connection to a flange (not shown) extending from the port or opening, for example. Alternatively, in any embodiment, the cover elements 68a-68c may comprise a thin layer of plastic film, metal foil, or the like, which overlays the opening and, optionally includes an adhesive coating (not shown) that removably secures the cover elements to the casing 100, as shown in FIGS. 1-4.

In any embodiment, one or more of the cover elements (cover elements 68a-68c) may be frangible. Thus, urging a detachment member through the second fluid pathway as described above further comprises urging the detachment member through the second cover element 68a and/or the third cover element 68b.

The porous carrier 30 permits allows solubilized and/or suspended constituents (e.g., cells, proteins, nucleic acids, salts) of a liquid sample to wick or flow longitudinally (e.g., laterally) from a sample-receiving zone toward a target cell-binding zone. Generally, the lateral flow device is in the form of a strip of the porous material (e.g. of 4-8 mm×40-80 mm in dimensions). Preferably, the porous material is composed of nitrocellulose membrane, polyvinylidene fluoride (PVDF), nylon or a single porous material matrix (e.g. FUSION 5™ (Whatman, Middlesex, UK), and as described in US Patent Application Publication No 2006/0040408), for example.

The sample-receiving zone 32 is the area of the porous carrier 30 onto which a sample-containing liquid (not shown) is applied and, once applied, the sample containing liquid moves longitudinally (e.g., via capillary action) therefrom through the carrier 30 toward the target cell-binding zone 34. Relative to vertical flow through a membrane filter, for example, the longitudinal movement of the sample through the porous carrier 30 advantageously provides improved separation of target cells (e.g., microorganisms) in the sample from particles (e.g., soil, dust, food particles, non-target cells) and/or molecules (e.g., proteins, fats, salts, chelating agents) that may otherwise inhibit or interfere with detection of the target cells or target molecules associated therewith. "Target molecules" and "target biomolecules", as used herein, refer to molecules that indicate the presence of a target cell in a sample. In the illustrated embodiment of FIGS. 1-4, the sample-receiving zone is accessible via the sample port 50.

In use, for example, the cover element 68c, if present, is moved or removed to expose the sample port 50 and a volume (e.g., a predetermined volume) of the sample-containing liquid can be poured or pipetted onto the exposed sample-receiving zone 32 of the porous carrier 30. Alternatively, the sample port 50 can be dipped into the sample (not shown) for a period of time sufficient to allow absorption of part of the sample into the porous carrier.

The target cell-binding zone 34 is a predetermined area of the porous carrier 30 that includes immobilized binding partners (e.g., antibodies, binding proteins, lectins, oligonucleotides). The binding partners (not shown) preferentially bind target molecules (e.g., surface proteins, lipopolysaccharide, peptidoglycan) that are linked to a target cell (e.g., a target microorganism). Thus, by forming a bond with a target molecule, the immobilized binding partner is immobilizing the target cell at the target cell-binding zone 34 of the porous carrier 30. The binding partners are immobilized to and/or in the porous carrier 30 using methods that are well known in the art. As the target cells (not shown) are carried through the target cell-binding zone 34 with the liquid migrating through the porous carrier 30, the target molecules bind to the binding partners, causing the target cell to become immobilized at the target cell-binding zone 34. Thus, the target cells are effectively concentrated at the target cell-binding zone of the sample preparation device 1000.

In any embodiment, the porous carrier of the present disclosure may be supported by a substrate. In any embodiment, the porous carrier further may be coupled (e.g., adhesively coupled) to the substrate. Advantageously, securing the porous carrier to a substrate can facilitate assembly of the device and facilitate alignment of the target cell-binding zone of the porous carrier with the first and second openings of the casing. Moreover, the substrate helps retain alignment of the target cell-binding zone with the first and second openings of the casing after the porous carrier contacts the liquid sample, which may cause swelling of the porous carrier.

Figure 5:
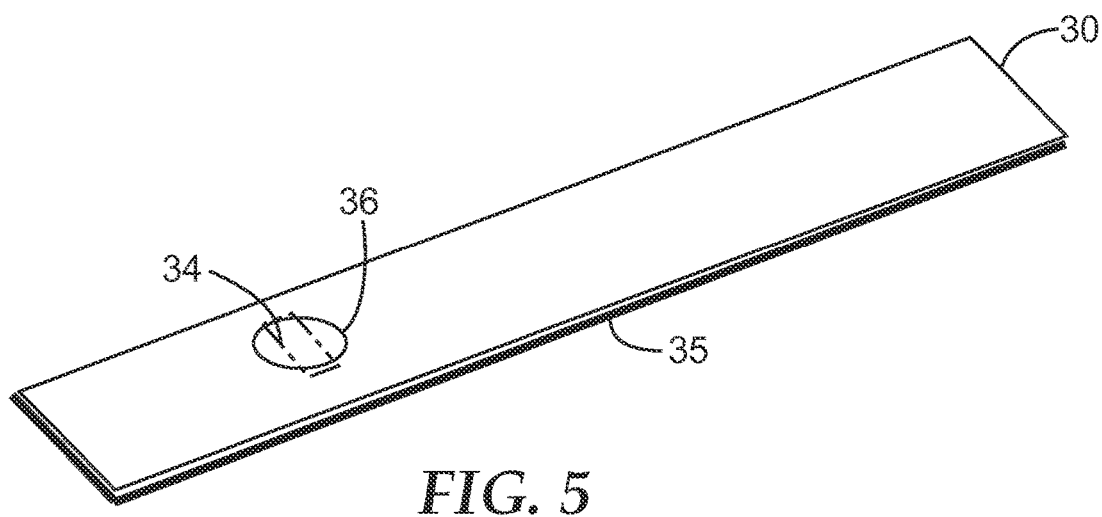
FIG. 5 is a perspective view of one embodiment of a porous carrier supported by a substrate according to the present disclosure.
Figure 6:
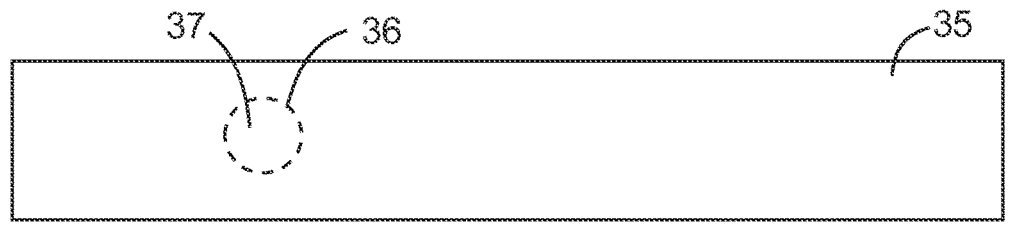
FIG. 6 is a bottom view of the substrate-supported porous carrier of FIG. 5.

FIGS. 5 and 6 show various views of one embodiment of a porous carrier 30 supported by a substrate 35. The substrate 35 can be fabricated using a material that is not water-absorbent. Suitable materials include, for example, glass, a plastic film, a metal foil, or combinations thereof. In any embodiment, the porous carrier 30 can be coupled (e.g., via an adhesive, not shown) to the substrate 35. In any embodiment, the substrate 35 may comprise an area of weakness 36 proximate the target cell-binding zone 34 of the porous carrier 30. The area of weakness 36 may include one or more scored segments, one or more frangible tie points, or perforations that facilitate separation of a part 37 of the substrate 35. In the assembled device, the area of weakness preferably is aligned with the second fluid pathway so that, when a detachment member is urged through the second fluid pathway, it detaches the part 37 of the substrate 35 along with a portion (not shown) or the entire target cell-binding zone 34 (shown as a shaded area in FIG. 5) of the porous carrier 30.

Returning to FIG. 1, in any embodiment, a sample preparation device of the present disclosure optionally can include a flow indicator 80 to indicate the liquid sample has moved through the porous carrier 30 from the sample-receiving zone 32 to or beyond the target cell-binding zone 34. Flow indicators 80 are known in the art of lateral-flow immunodiagnostic devices and may comprise, for example microparticles. The microparticles may comprise surface molecules (e.g., biotin) that are capable of binding to a corresponding binding partner (e.g., avidin) that is immobilized at a flow indicator control zone 38. Methods of immobilizing the binding partner to the porous carrier 30 are well known in the art. In addition, the microparticles may comprise a colored or fluorescent dye or pigment that is visually observable. The flow indicators 80 can be carried by the liquid sample through the porous carrier 30 to a flow indicator control zone 38. The flow indicator control zone 38 is a predefined area that is typically disposed on and/or in the porous carrier 30 at a location wherein the target cell-binding zone 34 is disposed between the sample-receiving zone 32 and the flow indicator control zone 38.

During use, the liquid sample migrates through the porous carrier 30 from the sample-receiving zone 32 toward and beyond the target cell-binding zone 34 and thereby moving the flow indicators 80 toward the flow indicator control zone 38. When the flow indicators 80 reach the flow indicator control zone 38, they bind to the corresponding binding partner, causing an observable accumulation (e.g., as a colored or fluorescent line or spot) of flow indicators 80.

Returning to FIG. 1, in any embodiment of a sample preparation device 1000 according to the present disclosure, the device optionally comprises one or more indicium 15. The indicium 15 can be aligned with the optional flow indicator control zone 38 of the porous carrier 30 and, thus indicate the location of the flow indicator control zone 38 which may otherwise not be distinguishable from other portions of the porous carrier 30 until the flow indicators 80 bind to the flow indicator control zone 38. In any embodiment, the casing of a sample preparation device may comprise an optional viewing window (not shown) proximate the flow-control binding zone in order to facilitate observation of the flow indicators bound thereto.

Figure 7:
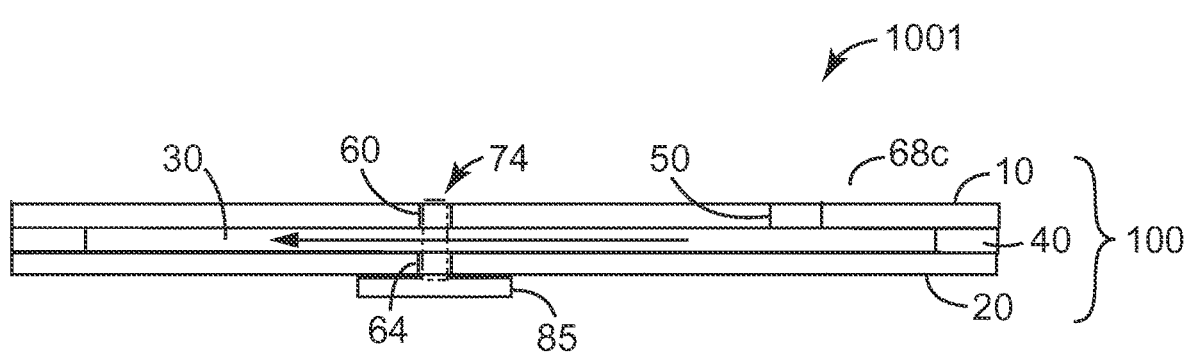
FIG. 7 is a cross-sectional side view of one embodiment of a sample preparation device that includes an absorbent body disposed adjacent the second opening.

In any embodiment, a sample preparation device of the present disclosure optionally can comprise an absorbent body disposed adjacent the second opening. FIG. 7 shows one embodiment of a sample preparation device 1001 comprising an absorbent body 85. The device 1001 comprises a casing 100 that includes a first piece 10, second piece 20, and optional spacer 40, each as described herein. The device 1001 further comprises a sample port 50, a first opening, 60, a second opening 64, and a second fluid pathway 74, each as described herein. The absorbent body 85 is disposed proximate the second opening 64 and is in fluid communication with the second fluid pathway 74. Accordingly, as a liquid (e.g., a wash solution) is urged through the target cell-binding zone (not shown in FIG. 7) of the porous carrier 30 via the second fluid pathway 74, the liquid is absorbed and retained by the absorbent body 85. In any embodiment, the absorbent body 85 optionally may be coupled (e.g., via an adhesive, not shown) to the casing 100. Additionally, or alternatively, the absorbent body 85 may be held in place by, and optionally coupled to, a cover element (e.g., third cover element 68b shown in the illustrated embodiment of FIG. 1) that covers the second opening 64.

The absorbent body 85 is spaced-apart from the porous carrier 30 such that the absorbent body is not in fluid communication with liquid that passes through the first fluid pathway 70 defined by the porous carrier. However, the absorbent body 85 is in fluid communication with the second fluid pathway 74 and, thus, receives liquids that are urged through the device 1001 via the second fluid pathway.

The absorbent body 85 can be fabricated using any absorbent material capable of absorbing a liquid (e.g., an aqueous liquid) urged through the device 1001 via the second fluid pathway 74. Non-limiting examples of suitable materials include foams (e.g., open-cell foams), sponges, gauze, cotton, and the like. In any embodiment, the material may comprise superabsorbent polymers (e.g., polyacrylate/polyacrylamide copolymers) and/or particles thereof.

Figure 8:
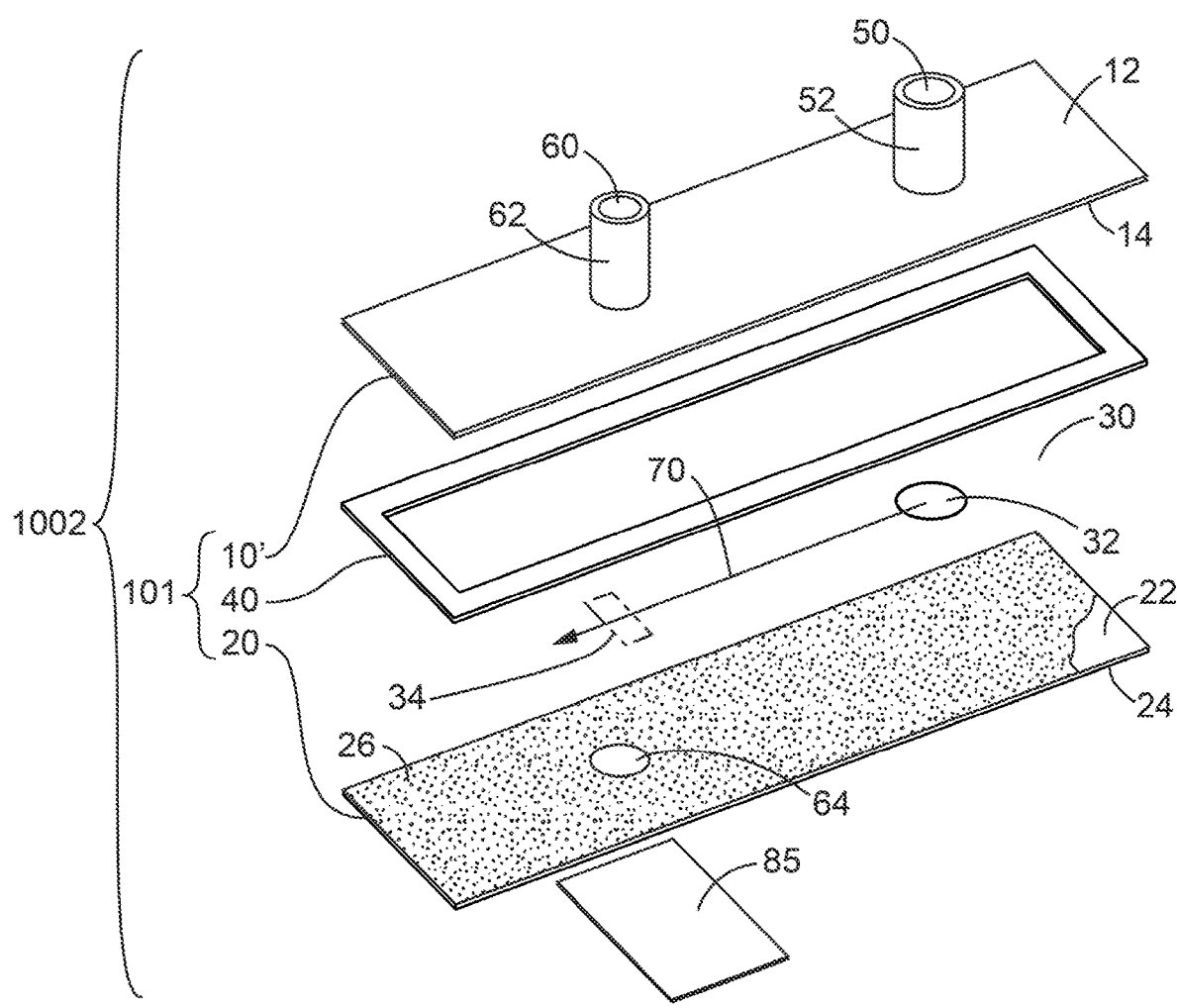
FIG. 8 is an exploded perspective view of one embodiment of a sample preparation device comprising a conduit for loading a sample and a conduit extending along a second fluid pathway according to the present disclosure.
Figure 9:
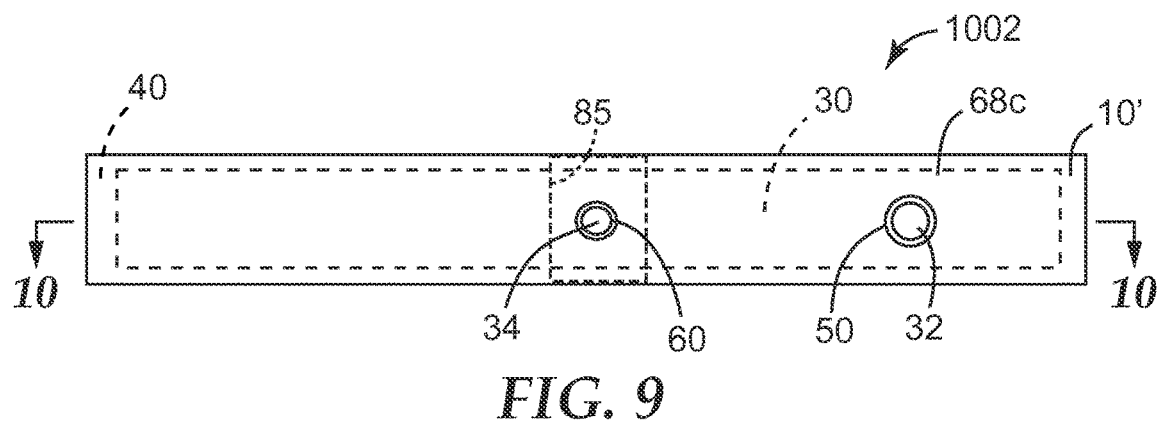
FIG. 9 is a plan view of the sample preparation device of FIG. 8.
Figure 10:
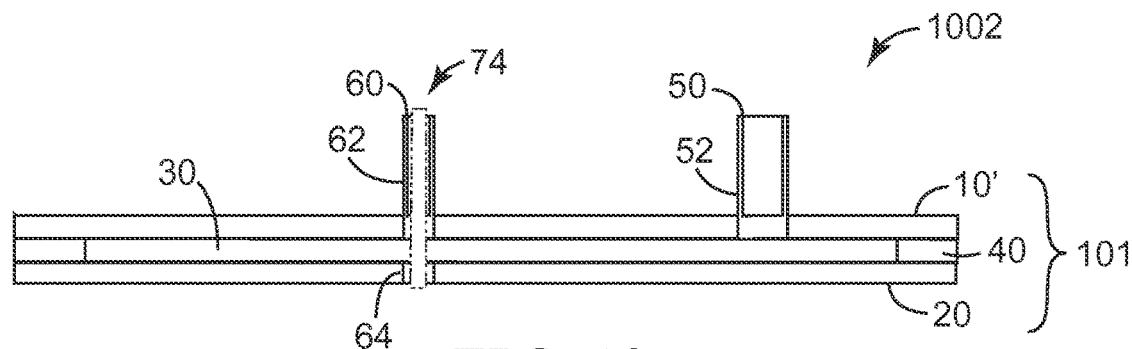
FIG. 10 is a cross-sectional side view of the device of FIG. 9, taken along line 10-10.

In any embodiment, a sample preparation device of the present disclosure optionally may comprise at least one conduit that extends from an opening to the porous carrier. FIGS. 8-10 show one embodiment of a sample preparation device 1002 comprising a plurality of conduits, each conduit extending from an opening in the casing 101 to the porous carrier 30. The casing 101 comprises a first piece 10', a second piece 20, and an optional spacer 40, as described herein. The porous carrier 30 comprises a sample-receiving zone 32, a target cell-binding zone 34, and defines a first liquid pathway 70 that extends from the sample-receiving zone 32 to and beyond the target cell-binding zone 34. The second piece 20 has a third side 22 and a fourth side 24 opposite the first side. The second piece 20 further comprises a second opening 64 and an optional adhesive layer 26 that can couple the second piece to the first piece 10' and/or the spacer 40, each as described herein. The device 1002 further comprises an absorbent body 85 disposed adjacent the second opening 64 outside the casing 101.

The first piece 10' of the sample preparation device 1002 comprises two conduits (e.g., first conduit 52 and second conduit 62, respectfully) extending therefrom. The optional first conduit 52 includes the sample port 50 at the end distal the casing 101. The first conduit 52 has an interior volume into which a liquid sample can be deposited (e.g., by pouring or pipetting). The interior volume is defined by the length and diameter of the first conduit 52 and, thus, may be adapted to hold any liquid volume that the operator desires to pass through the porous carrier 30. Advantageously, the first conduit 52 permits the operator to dispense a sample into the conduit and walk away while the liquid migrates into the porous carrier 30. In any embodiment, an optional third conduit (not shown) may extend from the second opening 64.

The optional second conduit 62 includes the first opening 60 at the end distal the casing 101. The second conduit 62 also has an interior volume into which a liquid can be deposited (e.g., by pouring or pipetting). A wash solution may be used, for example, to wash non-target biomolecules, debris, and/or chemicals that are present at the target cell-binding zone 34 but that are not specifically bound to the binding partner immobilized at the target cell-binding zone. The interior volume is defined by the length and diameter of the second conduit 62 and, thus, may be adapted to hold any liquid volume that the operator desires to pass through the porous carrier 30. Advantageously, the second conduit 62 permits the operator to dispense a liquid (e.g., a wash solution, an indicator reagent) into the first opening 60 and to pass the liquid through the porous carrier 30 via the second fluid pathway 74. For example, the liquid may be passed through the porous carrier 30 by negative pressure, by gravity flow or, alternatively, may be urged through the porous carrier via positive pressure using a detachment member as described herein.

It is particularly advantageous that a device of the present disclosure comprising a second conduit aligned with the second fluid pathway permits the operator to pass, in a plug-flow process, a substantial volume of wash solvent (relative to the void volume of the target cell-binding zone of the porous carrier) through the target cell-binding zone. For example, if the porous carrier is about 0.2 mm thick and the target cell-binding zone is disposed in an area approximately 6 mm$^2$, the void volume of the target cell-binding zone may be about 5-25 μL. In this example, passing 500 μL of wash solvent through the target cell-binding zone of the porous carrier results in washing the porous carrier with approximately 20-100 volumes of liquid. This results in substantial dilution and/or removal of unbound materials from the target cell-binding zone.

In any embodiment, a sample preparation device of the present disclosure further comprises an optional detachment member. FIG. 11A shows one embodiment of a sample preparation device 1003 comprising a detachment member 500 according to the present disclosure. The detachment member 500 is slideably engaged in the second fluid pathway 74 and may be used to detach a portion (e.g., a portion comprising the target cell-binding zone, not shown) of the porous carrier 30 and to expel the portion from the device 1003 as described herein. The detachment member 500 comprises a shaft 591 that comprises a tip 592. The shaft 591 is dimensioned to traverse at least the length of the second fluid pathway 74 from the first opening 60 to the second opening 64. In addition, the detachment member 500 optionally comprises a handle 595 that can be used to urge the tip 592 of the shaft 591 (e.g., using manual pressure) through the second fluid pathway 74 of the device 1003.

The detachment member 500 can be formed using processes that are well known in the art (e.g., extrusion or molding processes) from a variety of materials including, but not limited to, plastic, glass, wood, metal, and combinations thereof.

Figure 11B:
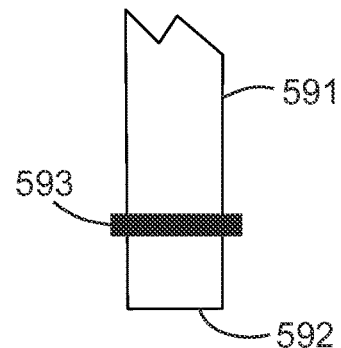
FIG. 11B is a detail view of the tip of the detachment member of FIG. 11A.
Figure 11A:
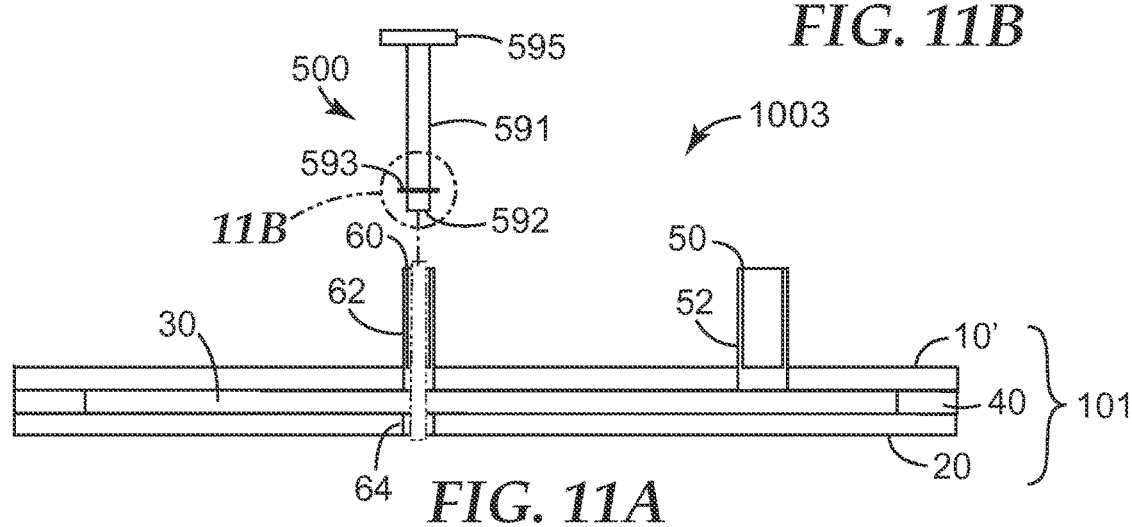
FIG. 11A is a partially-exploded cross-sectional side view of a sample preparation device comprising a detachment member according to the present disclosure.

FIG. 11B shows a detailed view of the tip 592 of the detachment member 500 of FIG. 11A. In any embodiment, the tip may be configured to form a substantially liquid-tight seal with the second conduit 62 of the device. Advantageously, in these embodiments, the detachment member 500 can be used to urge a liquid (not shown) disposed in the second conduit 62 through the second fluid pathway 74. In any embodiment, the shaft 591 of the detachment member 500 may comprise an optional seal 593 (e.g., a rubber O-ring) to facilitate slideable contact between the detachment member 500 and the walls of the second conduit 62.

In any embodiment, the tip 592 of the detachment member 500 may be configured to facilitate detachment of a portion of the porous carrier of the sample preparation device (i.e., the tip 592 may comprise a cutting structure). For example, the tip 592 may be concave (not shown), thereby forming a perimeter edge that facilitates cutting the porous carrier. Alternatively, the tip 592 may comprise cutting features (e.g., a serrated edge, not shown) that facilitates cutting the porous carrier. Alternatively, the tip 592 may be substantially devoid of cutting features (i.e., the tip 592 may be blunt).

Figure 12A:
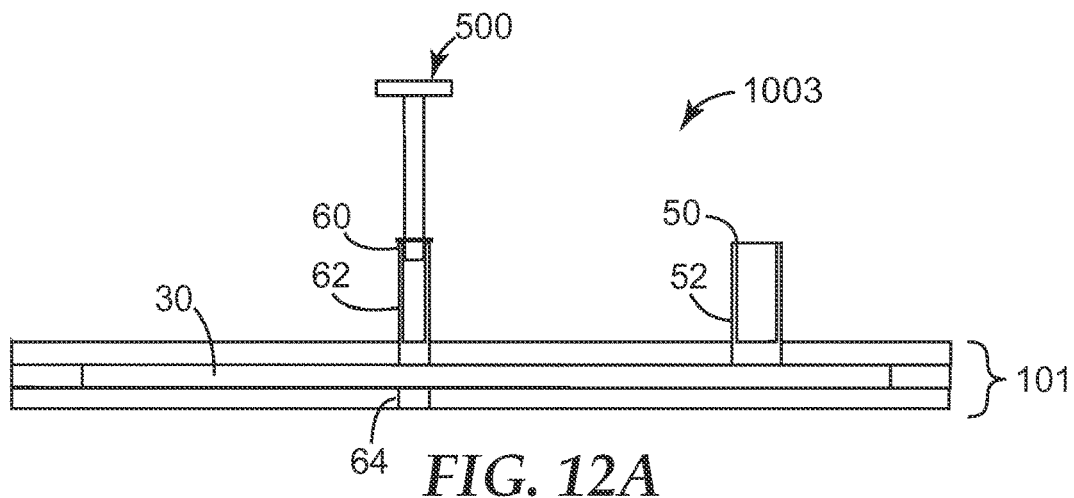
FIG. 12A is a side view, partially in section, of the sample preparation device of FIG. 10 comprising a detachment member disposed in a first operational position therein.
Figure 12B:
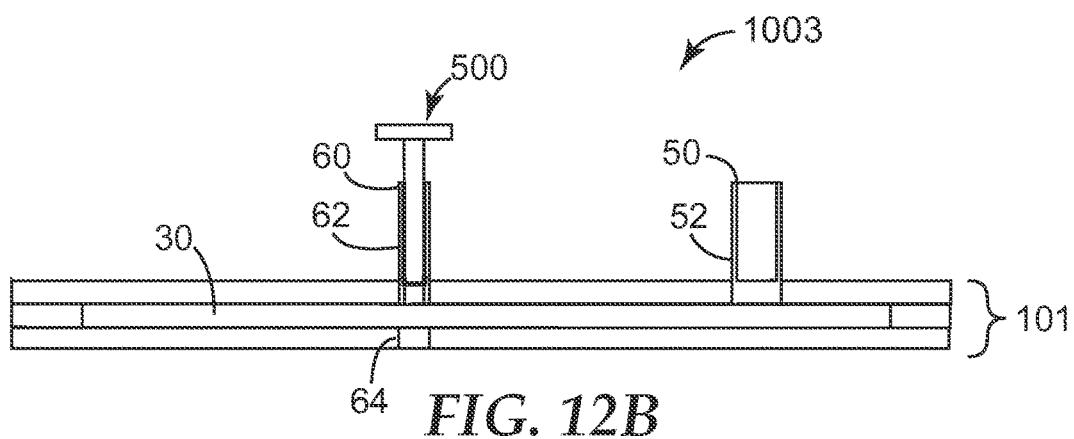
FIG. 12B is a side view, partially in section, of the sample preparation device of FIG. 10 comprising a detachment member disposed in a second operational position therein.
Figure 12C:
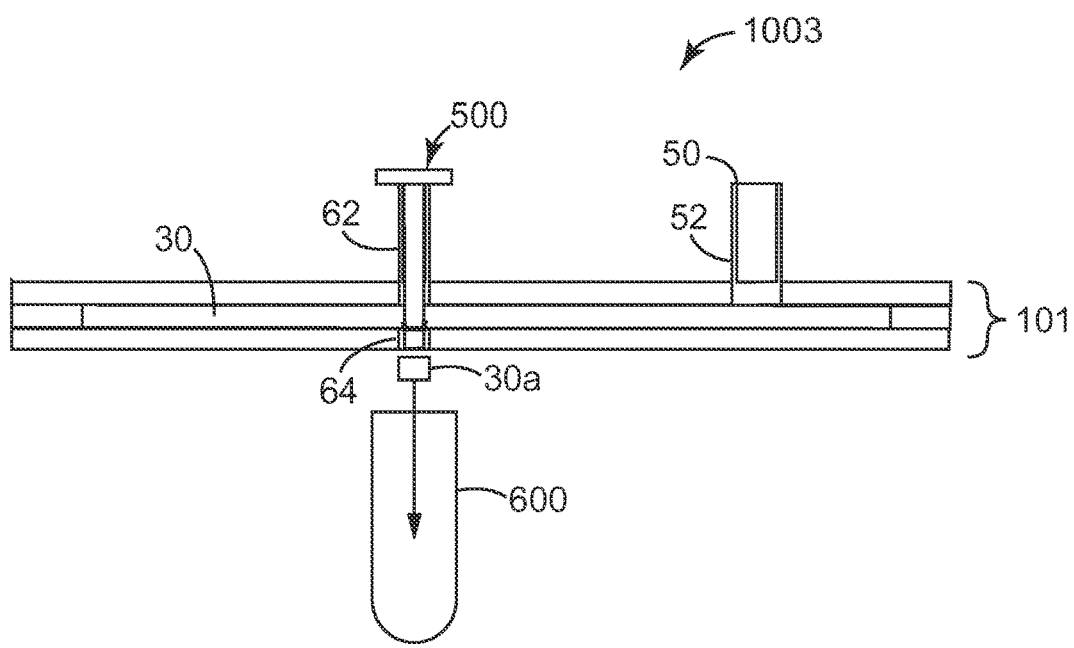
FIG. 12C is a side view, partially in section, of the sample preparation device of FIG. 10 comprising a detachment member disposed in a third operational position therein.
Figure 13:
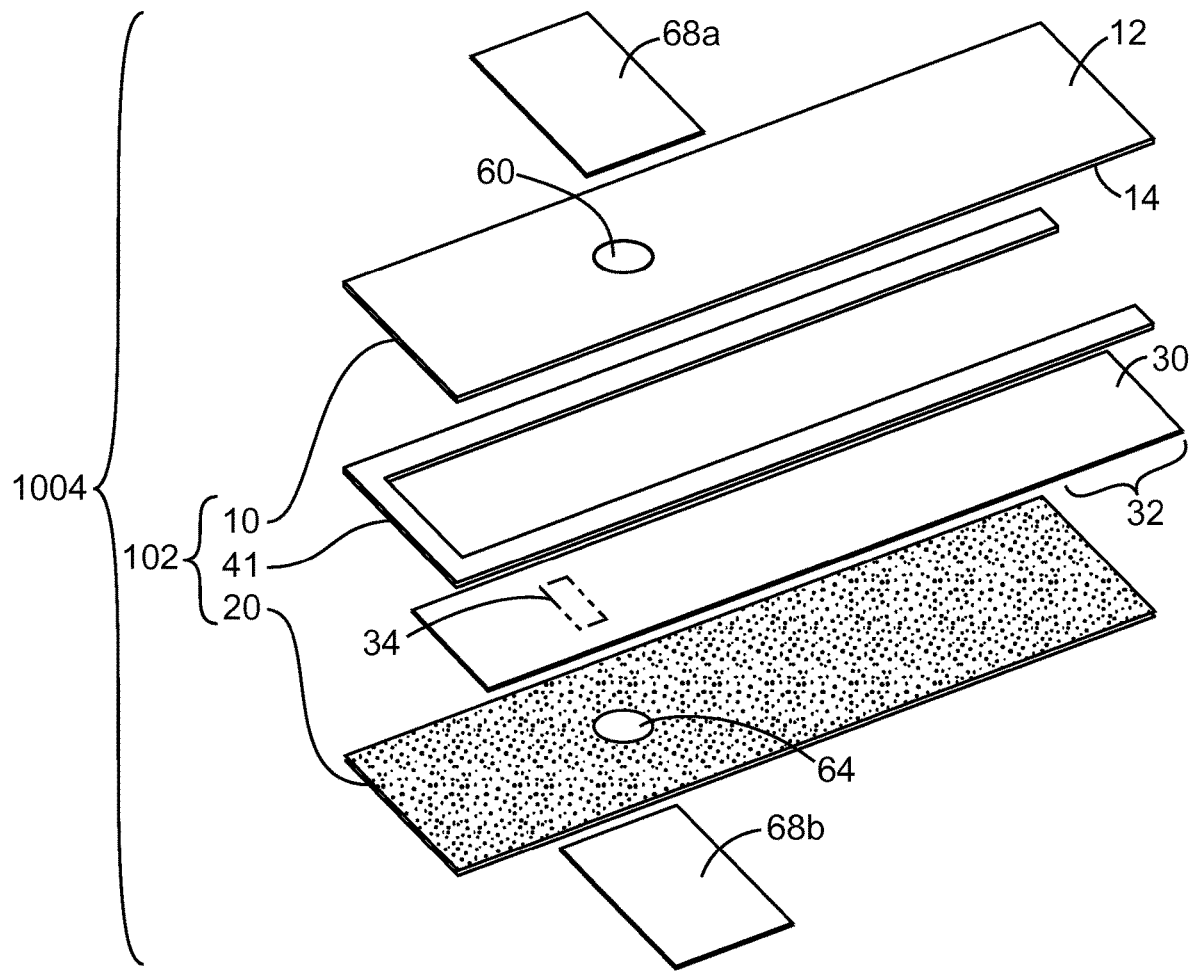
FIG. 13 is a partially exploded perspective view of a sample preparation device that comprises a porous carrier having a sample-receiving zone that extends outside the casing according to the present disclosure.
Figure 14:
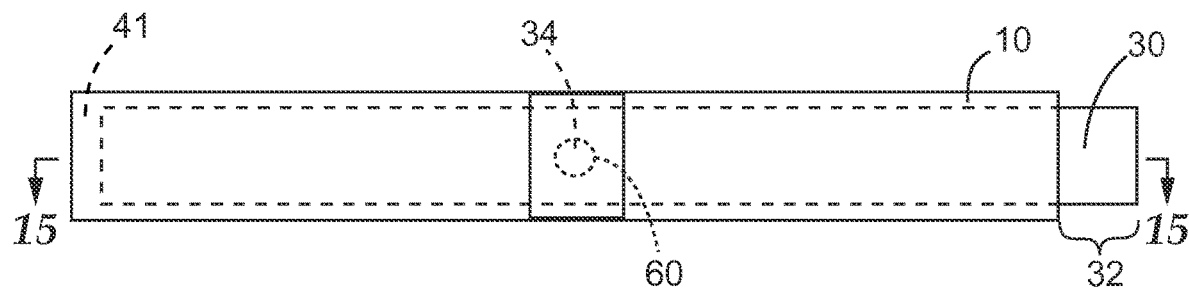
FIG. 14 is a plan view of the device of FIG. 13.
Figure 15:
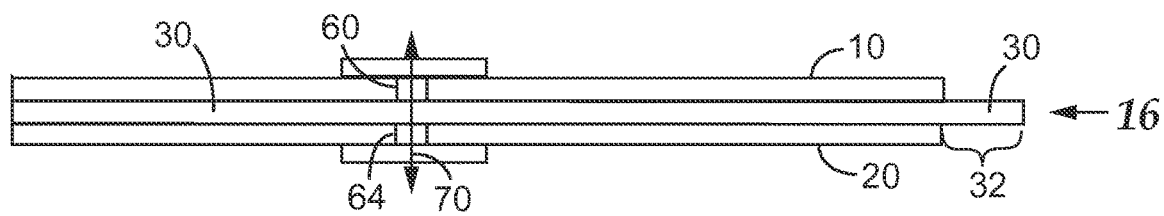
FIG. 15 is a cross-sectional side view of the device of FIG. 14, taken along line 15-15.
Figure 16:
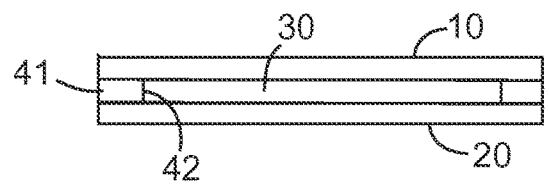
FIG. 16 is a side view of the device of FIG. 15.

A detachment member can be used to perform a plurality of functions in a sample processing device of the present disclosure. Accordingly, the various functions may be accomplished by moving the detachment member from one operational position to another with respect to the casing of the sample preparation device. FIGS. 12A-12C illustrate several operational positions of the detachment member in a sample processing device of the present disclosure.

FIG. 12A shows one embodiment of a detachment member 500 disposed in a first operational position with respect to a sample preparation device 1003. The device 1003 of the illustrated embodiment comprises a casing 101 that encases a porous carrier 30 as disclosed herein. The casing 101 includes a having a first opening 60 on one side and a second opening 64 opposite the first opening, as described herein. The first opening is disposed at the end of a second conduit 62 extending from the casing 101 as described herein. In this embodiment, the tip (i.e., tip 592 of the shaft 591 as shown in FIG. 11A) of the detachment member 500 is slideably engaged in the first opening 60 of the device 1003. In the first operational position, the detachment member functions as a closure to prevent external material from entering the device 1003 through the first opening 60 and potentially contaminating or otherwise interfering with a portion (e.g., the target cell-binding zone, not shown) of the porous carrier 30 of the sample preparation device 1003.

FIG. 12B shows the sample preparation device 1003 of FIG. 12A with the detachment member 500 disposed in a second operational position (i.e., with the tip of the detachment member disposed adjacent the porous carrier 30). The movement of the detachment member 500 from the first operational position to the second operational position can accomplish at least two functions: i) moving the detachment member positions the detachment member 500 proximate the porous carrier 30 prior to using the detachment member to cut and/or detach a portion of the porous carrier, and ii) moving the detachment member can urge a liquid (e.g., a wash liquid as described herein), if present in the interior volume of the second conduit 62, through the porous carrier via the second fluid pathway (second fluid pathway 74 shown in FIG. 11A). By urging a liquid through the porous carrier via the second fluid pathway, the operator can dilute or wash out non-target particles and/or molecules (e.g., proteins, fats, nucleic acids, salts, chelating agents) that may otherwise inhibit or interfere with detection of the target cells in a subsequent step of the method.

FIG. 12C shows the sample preparation device 1003 of FIG. 12A with the detachment member 500 disposed in a third operational position (i.e., with the tip of the detachment member disposed proximate the second opening 64). The movement of the detachment member 500 from the first or second operational position to the third operational position functions to detach a portion (detached portion 30a, which may comprise at least part of or the entire target cell-binding zone of the porous carrier 30, for example) of the porous carrier. In addition, movement of the detachment member 500 to the third operational position optionally expels the detached portion 30a of the porous carrier from the casing 101 for further processing to detect a target molecule associated with the target cell. FIG. 12C also shows a receptacle 600 (e.g., a reaction tube) which can be positioned proximate the second opening 64 and into which the detached portion 30a can be expelled by the detachment member 500.

In any embodiment, the sample preparation device can be specifically adapted for obtaining a sample by dipping only the sample-receiving portion into a liquid sample. FIGS. 13-16 show various views of one embodiment of a sample preparation device 1004 specifically adapted for obtaining a sample by dipping. The device 1004 comprises a casing 102 that includes a first piece 10 and a second piece 20, both as described herein, and an optional spacer 41. The optional spacer a41 includes an open end 42. The device 1004 comprises a porous carrier 30 that includes a target cell-binding zone 34 as described herein. The sample-receiving zone 32 of the porous carrier 30 extends through the open end 42 of the spacer 41 and outside the casing 102. Thus, the sample receiving zone 32 can be dipped readily into a liquid sample (not shown) in order for the sample to move into and through the porous carrier 30. The device 1004 comprises a first opening 60 and second opening 64 that form the termini of the second fluid pathway 74 as described herein.

In another aspect, the present disclosure provides a kit for detecting a target cell in a sample. The kit can comprise any embodiment of the sample preparation device disclosed herein. In any embodiment, the kit further comprises any embodiment of a detachment member described herein. The detachment member is dimensioned to traverse the latent passageway from the first opening to the second opening, as described herein. In any embodiment, the detachment member is slideably engaged in the second fluid pathway of the sample preparation device. In any embodiment, the detachment member is configured to urge an aqueous liquid through the casing (e.g., through a second conduit of the casing). In any embodiment, the kit further comprises a wash liquid and/or a reagent for nucleic acid amplification (e.g., a primer, a ribonucleotide triphosphate, a deoxyribonucleotide triphosphate, a polymerase enzyme). In any embodiment, the kit can comprise a release solution as described hereinbelow.

In another aspect the present disclosure provides a first method of detecting a target cell (e.g., a target microorganism) in a sample. The first method comprises contacting a liquid sample with the porous carrier of any embodiment of the sample preparation device disclosed herein. In any embodiment of the first method, the sample preparation device comprises a casing comprising a first and second opening, and a porous carrier. The porous carrier comprises a sample-receiving zone at a first predefined location and a target cell-binding zone at a second predefined location spaced apart from the first predefined location. In addition, the porous carrier defines a first fluid pathway extending between the sample-receiving zone and the target cell-binding zone. At least portion of the porous carrier is disposed in the casing. A second fluid pathway extends through the casing from the first opening and the second opening, the second fluid pathway intersecting the porous carrier at the target cell-binding zone.

In any embodiment of the first method, contacting a liquid sample with a porous carrier comprises contacting the liquid sample with a sample-receiving zone of the porous carrier, as described herein. In any embodiment of the first method, contacting a liquid sample with a porous carrier comprises contacting a liquid sample from an enrichment culture with the porous carrier (e.g., at the sample-receiving zone). Advantageously, a portion of an enrichment culture can be loaded directly into the sample preparation device and target cells (e.g., microorganisms) present in the enrichment culture can be captured at the target cell-binding zone for further analysis as described herein.

The first method further comprises the steps of allowing at least a portion of the liquid sample to move (e.g., longitudinally) through the porous carrier from the sample-receiving zone at least to the target cell-binding zone; after the at least a portion of the liquid has moved to the target cell-binding zone, urging a detachment member through the second fluid pathway from the first opening to the second opening and thereby expelling a portion of or the entire target cell-binding zone; and processing the portion of the target cell-binding zone to detect an indication of the target microorganism.

As the liquid moves to the target cell-binding zone, it carries target cells, if a target cell is present in the sample, through the porous carrier. In addition, the liquid may carry other particles (e.g., soil, dust, food particles, non-target cells) and molecules (e.g., proteins, fats, nucleic acids, salts, chelating agents) that are not associated with the target cell. These non-target particles and molecules potentially may interfere with analytical processes (e.g., nucleic acid amplification processes) that may be used later to detect target cells present in the sample.

As the liquid sample migrates through the target cell-binding zone of the porous carrier, the target cells, if present, may bind to binding partners (e.g., antibodies, lectins, nucleic acids) attached to the porous carrier at the target cell-binding zone as described herein. At least some of the non-target particles and molecules present in the sample may be retarded, relative to the target cells, as the liquid passes through the porous carrier and, thus, do not co-accumulate with the target cells at the target cell-binding zone. In addition, at least some of the non-target particles and molecules continue to flow with the liquid past the target cell-binding zone, thereby separating these non-target particles and molecules from the target cells. Accordingly, the first method separates the target cells, if present, from non-target particles and molecules that might interfere with or otherwise inhibit a process (e.g., a nucleic acid amplification detection process) used to detect the target cells.

In any embodiment of the first method, after the at least a portion of the liquid has moved through the sample preparation device to the target cell-binding zone, the method comprises urging a detachment member through the second fluid pathway from the first opening to the second opening and thereby detaching and expelling a portion of the target cell-binding zone. In any embodiment of the first method, detaching and expelling a portion of the target cell-binding zone can comprise detaching and expelling the entire target cell-binding zone.

Processing the portion of the target cell-binding zone to detect an indication of the target microorganism can be performed using any suitable detection process known in the art including, but not limited to, culture methods, biochemical methods (e.g., detection of enzyme activities that are associated with the target microorganism), immunological methods (e.g., immunostaining, ELISA), histological methods (e.g., histological stains), and genetic methods (e.g., nucleic acid amplification, hybridization). In any embodiment, amplifying a nucleic acid sequence can comprise amplifying a nucleotide sequence associated with the target microorganism. A particularly preferred method of nucleic acid amplification includes the isothermal DNA amplification and bioluminescence detection method embodied in the 3M™ Molecular Detection System available from 3M Company (St. Paul, Minn.).

In any embodiment of the first method, after the at least a portion of the liquid has moved to the target cell-binding zone, the method optionally further can comprise passing a wash solvent through the porous carrier via the second fluid pathway. The purpose of the wash solution is to wash out of the target cell-binding zone any unbound impurities (e.g., particles (e.g., soil, dust, food particles, non-target cells) and/or molecules (e.g., proteins, fats, nucleic acids, salts, chelating agents) that are not associated with the target cell. Passing a wash solvent through the porous carrier may be performed, for example, by urging (e.g., via a syringe or pipet) a wash solvent (e.g., sterile water, a buffer solution) through the second fluid pathway. Advantageously, because the second fluid pathway of the sample preparation device is oriented orthogonal to the first fluid pathway, the wash solvent washes unbound materials (e.g., proteins, nucleic acids, cell fragments, food particles, salts) out of the target cell-binding zone of porous carrier, thereby eliminating materials that might otherwise interfere with the detection of target analytes bound to the target cell-binding zone. When a second conduit is present in the device as described herein, the wash solvent can be loaded into the second conduit and the solvent can be urged through the porous carrier by gravity flow, for example, or via positive pressure exerted on the liquid via a plunger or a detachment member as described herein. This optional step can significantly reduce the quantity of substances that were in the original sample that might interfere with or otherwise reduce the sensitivity of the subsequent process of processing the portion of the target cell-binding zone to detect an indication of the target microorganism.

In any embodiment of the first method, passing a wash solvent through the porous carrier via the second fluid pathway can be performed before or after the portion of the porous carrier has been ejected from the sample processing device.

In an alternative embodiment (not shown), a source of negative pressure (e.g., a vacuum hose) can be operationally applied to the second opening in order to draw the wash solvent through the second fluid pathway.

In any embodiment of the first method of the present disclosure, the method optionally comprises treating the expelled portion of the porous carrier, or any cells released therefrom, to cause cell lysis. A variety of suitable means for causing cell lysis are known in the art and include, but are not limited to, physical lysis methods (e.g., boiling, sonication, cavitation via French press) and chemical lysis methods (e.g., contacting the sample with detergents, surfactants, quaternary amines, chaotropic reagents, or organic solvents). Accordingly, the expelled portion of the porous carrier, or any cells eluted therefrom, can be treated with a means for causing cell lysis in order to release a detectable biomolecule (e.g., an interior or exterior biomolecule such as a protein, an enzyme, a polysaccharide, a nucleic acid) that indicates the presence of the target cell or in order to permeabilize the cell to provide access for detection moiety (e.g., a primer, a polymerase, a labeled antibody) to interact with a detectable molecule within the cell. Advantageously, the target cells may be lysed in situ (i.e., in the ejected portion of the porous carrier) or, alternatively, the cells may be released from the target cell-binding zone of the porous carrier before being treated to cause cell lysis.

Cells may be released from the target cell binding zone by any suitable method known in the art. For example, if the binding partner that captures the target cells is an antibody, the target cells may be released by contacting the ejected portion of the target cell-binding zone with a suitable release solution (e.g., an aqueous solution having the appropriate pH and/or ionic strength to cause release of the target cell antigen that is bound to the antibody). Thus, as the release solution passes through a target cell-binding zone to which a target cell is bound, the target cell is released into the release solution.

In any embodiment, the first method further can comprise positioning a receptacle proximate the second opening. In any embodiment, the receptacle can be substantially free of biological material. In these embodiments, urging a detachment member through the second fluid pathway to detach at least a portion of the target cell-binding zone further can comprise moving a portion (e.g., at least a part of or the entire target cell-binding zone) of the porous carrier into the receptacle, as shown in FIG. 12C. Advantageously, performing a transfer of the portion of the porous carrier in this manner can eliminate the possibility of contact between the portion of the porous carrier and potential sources of biological material external to the casing. A preferred method of processing the expelled portion of the target cell-binding zone includes processing the portion using the Molecular Detection System (hereinafter, "MDS") available from 3M Company (St. Paul, Minn.). Accordingly, the portion of the target cell-binding can be expelled directly into the MDS lysis tube and an aliquot of the resulting lysate can be processed to amplify and detect a nucleic acid that indicates the presence of the target microorganism.

In another aspect the present disclosure provides a second method of detecting a target cell (e.g., a target microorganism) in a sample. The second method comprises contacting a liquid sample with the porous carrier of any embodiment of the sample preparation device disclosed herein. In any embodiment of the second method, the sample preparation device comprises a casing comprising a first and second opening, and a porous carrier. The porous carrier comprises a sample-receiving zone at a first predefined location and a target cell-binding zone at a second predefined location spaced apart from the first predefined location. In addition, the porous carrier defines a first fluid pathway extending between the sample-receiving zone and the target cell-binding zone. At least portion of the porous carrier is disposed in the casing. A second fluid pathway extends through the casing from the first opening and the second opening, the second fluid pathway intersecting the porous carrier at the target cell-binding zone.

In any embodiment of the second method, contacting a liquid sample with a porous carrier comprises contacting the liquid sample with a sample-receiving zone of the porous carrier, as described herein. In any embodiment of the second method, contacting a liquid sample with a porous carrier comprises contacting a liquid sample from an enrichment culture with the porous carrier (e.g., at the sample-receiving zone). Advantageously, a portion of an enrichment culture can be loaded directly into the sample preparation device and target cells (e.g., microorganisms) present in the enrichment culture can be captured at the target cell-binding zone for further processing and analysis as described herein.

The second method further comprises the steps of allowing at least a portion of the liquid sample to move (e.g., longitudinally) through the porous carrier from the sample-receiving zone at least to the target cell-binding zone; after the at least a portion of the liquid has moved to the target cell-binding zone, urging a release solution through the second fluid pathway and thereby expelling from the device a part of the release solution comprising a target microorganism, if present in the second fluid pathway; and processing the portion of the target cell-binding zone to detect an indication of the target microorganism.

As the liquid moves to the target cell-binding zone, it carries target cells, if a target cell is present in the sample, through the porous carrier. In addition, the liquid may carry other particles (e.g., soil, dust, food particles, non-target cells) and molecules (e.g., proteins, fats, nucleic acids, salts, chelating agents) that are not associated with the target cell. These non-target particles and molecules potentially may interfere with analytical processes (e.g., nucleic acid amplification processes) that may be used later to detect target cells present in the sample.

As the liquid sample migrates through the target cell-binding zone of the porous carrier, the target cells, if present, may bind to binding partners (e.g., antibodies, lectins, nucleic acids) attached to the porous carrier at the target cell-binding zone as described herein. At least some of the non-target particles and molecules present in the sample may be retarded, relative to the target cells, as the liquid passes through the porous carrier and, thus, do not co-accumulate with the target cells at the target cell-binding zone. In addition, at least some of the non-target particles and molecules continue to flow with the liquid past the target cell-binding zone, thereby separating these non-target particles and molecules from the target cells. Accordingly, the second method separates the target cells, if present, from non-target particles and molecules that might interfere with or otherwise inhibit a process (e.g., a nucleic acid amplification detection process) used to detect the target cells.

Thus, in any embodiment of the second method, after the at least a portion of the liquid has moved to the target cell-binding zone, the method optionally comprises passing a wash solvent through the porous carrier via the second fluid pathway. The purpose of the wash solution is to wash out of the target cell-binding zone any unbound impurities (e.g., particles (e.g., soil, dust, food particles, non-target cells) and/or molecules (e.g., proteins, fats, nucleic acids, salts, chelating agents) that are not associated with the target cell. Passing a wash solvent through the porous carrier may be performed, for example, by urging (e.g., via a syringe or pipet) a wash solvent (e.g., sterile water, a buffer solution) through the second fluid pathway. Advantageously, because the second fluid pathway of the sample preparation device is oriented orthogonal to the first fluid pathway, the wash solvent washes unbound materials (e.g., proteins, nucleic acids, cell fragments, food particles, salts) out of the target cell-binding zone of porous carrier, thereby eliminating materials that might otherwise interfere with the detection of target cells bound to the target cell-binding zone. When a second conduit is present in the device as described herein, the wash solvent can be loaded into the second conduit and the solvent can be urged through the porous carrier by gravity flow, for example, or via positive pressure exerted on the liquid via a plunger or a detachment member as described herein. This optional step can significantly reduce the quantity of substances that were in the original sample that might interfere with or otherwise reduce the sensitivity of the subsequent process of processing the portion of the target cell-binding zone to detect an indication of the target microorganism.

In an alternative embodiment (not shown), a source of negative pressure (e.g., a vacuum hose) can be operationally applied to the second opening in order to draw the wash solvent through the second fluid pathway.

The second method of the present disclosure comprises urging a release solution through the second fluid pathway and thereby expelling from the device in a part of the release solution comprising a target microorganism, if present in the second fluid pathway. Cells are released from the target cell binding zone using any suitable release solution known in the art. For example, if the binding partner that captures the target cells is an antibody, the target cells may be released by urging (e.g., via positive pressure, negative pressure, or gravity flow) a suitable release solution (e.g., an aqueous solution having the appropriate pH and/or ionic strength to cause release of the target cell antigen that is bound to the antibody) through the second fluid pathway and collecting (e.g., in a reaction tube) the part of the release solution that exits the second fluid pathway via the second opening. Thus, as the release solution passes through a target cell-binding zone to which a target cell is bound, the target cell is released into the release solution and is collected with the release solution that exits the device via the second opening.

In any embodiment, the second method further can comprise positioning a receptacle proximate the second opening. In any embodiment, the receptacle can be substantially free of biological material. In these embodiments, urging a release solution through the second fluid pathway and thereby expelling from the device in a part of the release solution comprising a target microorganism, if present in the second fluid pathway further can comprise collecting a part of the release solution as it exits the sample processing device via the second opening (not shown). Advantageously, collecting a part of the release solution in this manner can eliminate the possibility of contact between the release solution exiting the sample preparation device and potential sources of biological material external to the casing of the device. A preferred method of processing the collected release solution includes processing the collected solution (and target cells therein) using the Molecular Detection System (hereinafter, "MDS") available from 3M Company (St. Paul, Minn.). Accordingly, the collected release solution can be expelled directly into the MDS lysis tube and an aliquot of the resulting lysate can be processed to amplify and detect a nucleic acid that indicates the presence of the target microorganism.

In any embodiment of the second method of the present disclosure, the method optionally comprises lysing the cells released by the release solution. A variety of suitable means for causing cell lysis are known in the art and include, but are not limited to, physical lysis methods (e.g., boiling, sonication, cavitation via French press) and chemical lysis methods (e.g., contacting the sample with detergents, surfactants, quaternary amines, chaotropic reagents, or organic solvents). Accordingly, the cells released by the release solution can be treated with a means for causing cell lysis in order to release a detectable biomolecule (e.g., an interior or exterior biomolecule such as a protein, an enzyme, a polysaccharide, a nucleic acid) that indicates the presence of the target cell or in order to permeabilize the cell to provide access for detection moiety (e.g., a primer, a polymerase, a labeled antibody) to interact with a detectable molecule within the cell.

In any embodiment of the second method, processing the cells released by the release solution to detect an indication of the target microorganism can be performed using any suitable detection process known in the art including, but not limited to, culture methods, biochemical methods (e.g., detection of enzyme activities that are associated with the target microorganism), immunological methods (e.g., immunostaining, ELISA), histological methods (e.g., histological stains), and genetic methods (e.g., nucleic acid amplification, hybridization). In any embodiment, amplifying a nucleic acid sequence can comprise amplifying a nucleotide sequence associated with the target microorganism. A particularly preferred method of nucleic acid amplification includes the isothermal DNA amplification and bioluminescence detection method embodied in the 3M™ Molecular Detection System available from 3M Company (St. Paul, Minn.).

EXEMPLARY EMBODIMENTS

Embodiment A is a method of detecting a target cell, comprising:

contacting a liquid sample with a porous carrier of a sample preparation device, the device comprising:
a casing comprising a first and second opening; and
the porous carrier;
wherein the porous carrier comprises a sample-receiving zone at a first predefined location and a target cell-binding zone at a second predefined location, the porous carrier defining a first fluid pathway extending from the sample-receiving zone through the target cell-binding zone;
wherein at least portion of the porous carrier is disposed in the casing;
wherein a second fluid pathway extends through the casing from the first opening to the second opening, the second fluid pathway intersecting the porous carrier at the target cell-binding zone;
allowing at least a portion of the liquid sample to move longitudinally through the porous carrier from the sample-receiving zone toward the target cell-binding zone;
after the at least a portion of the liquid has moved to the target cell-binding zone, urging a detachment member through the second fluid pathway from the first opening to the second opening and thereby expelling a portion of the target cell-binding zone; and
processing the portion of the target cell-binding zone, or a cell released therefrom, to detect an indication of the target cell.

Embodiment B is the method of Embodiment A, wherein the device further comprises a first cover element that covers the first opening or a second cover element that covers the second opening, wherein urging a detachment member through the second fluid pathway comprises urging the detachment member through the first cover element or the second cover element.

Embodiment C is the method of any one of the preceding Embodiments, wherein the carrier is supported by a substrate, wherein urging a detachment member through the second fluid pathway to detach at least a portion of the target cell-binding zone further comprises using the detachment member to detach a portion of the substrate.

Embodiment D is a method of detecting a target cell
contacting a liquid sample with a porous carrier of a sample preparation device, the device comprising:
a casing comprising a first and second opening; and
the porous carrier;
wherein the porous carrier comprises a sample-receiving zone at a first predefined location and an target cell-binding zone at a second predefined location, the porous carrier defining a first fluid pathway extending from the sample-receiving zone through the target cell-binding zone;
wherein at least portion of the porous carrier is disposed in the casing;
wherein a second fluid pathway extends through the casing from the first opening and the second opening, the second fluid pathway intersecting the porous carrier at the target cell-binding zone;
allowing at least a portion of the liquid sample to move longitudinally through the porous carrier from the sample-receiving zone toward the target cell-binding zone;
after the at least a portion of the liquid has moved to the target cell-binding zone, urging a release solution through the second fluid pathway and thereby expelling from the device a part of the release solution comprising a target microorganism, if present in the second fluid pathway; and
processing the part of the release solution to detect an indication of the target microorganism.

Embodiment E is the method of any one of the preceding Embodiments wherein, after the at least a portion of the liquid has moved to the target cell-binding zone, the method further comprises a step of passing a wash solvent through the porous carrier via the second fluid pathway.

Embodiment F is the method of any one of the preceding Embodiments, further comprising positioning a receptacle proximate the second opening, wherein expelling a portion of the target cell-binding zone or expelling the part of the release solution further comprises moving the portion of the target cell-binding zone or moving the part of the release solution into the receptacle.

Embodiment G is the method of any one of the preceding Embodiments, wherein contacting a liquid sample with a porous carrier comprises contacting a liquid sample from an enrichment culture with the porous carrier.

Embodiment H is the method of any one of the preceding Embodiments, wherein processing the portion of the analyte-binding zone or processing the part of the release solution to detect an indication of the target microorganism further comprises processing the portion of the analyte-binding zone or processing the part of the release solution to detect a biomolecule associated with the target cell.

Embodiment I is the method of Embodiment G, wherein detecting a biomolecule associated with the target cell comprises detecting a nucleic acid, an enzyme, or an antigenic biomolecule.

Embodiment J is the method of any one of the preceding Embodiments, wherein processing the portion of the target cell-binding zone or processing the part of the release solution comprises amplifying a nucleic acid sequence, wherein the nucleic acid sequence comprises a nucleotide sequence associated with the target cell.

Embodiment K is the method of any one of the preceding Embodiments, wherein the method of detecting a target cell is a method of detecting a target microorganism.

Embodiment L is a device, comprising:
a casing comprising an interior, a first opening, and a second opening; and
a porous carrier comprising a sample-receiving zone and a target cell-binding zone;
wherein the porous carrier defines a first fluid pathway that extends from the sample-receiving zone to the target cell-binding zone;
wherein at least portion of the porous carrier is disposed in the interior of the casing;
wherein a second fluid pathway comprising a central axis extends through the casing from the first opening and the second opening, the second fluid pathway intersecting the porous carrier at the target cell-binding zone;
wherein the central axis is oriented orthogonal to the first fluid pathway.

Embodiment M is the device of Embodiment L, further comprising a sample port that provides access to the sample-receiving zone, wherein the sample-receiving zone is disposed in the interior of the casing.

Embodiment N is the device of Embodiment L or Embodiment M, wherein the casing further comprises a first conduit that extends from the sample port to the interior of the casing.

Embodiment O is the device of any one of Embodiments L though N, wherein the casing further comprises a second conduit that extends from the first opening to the interior of the casing.

Embodiment P is the device of any one of Embodiments L through O, further comprising a flow indicator disposed in the porous carrier in the first fluid pathway.

Embodiment Q is the device of Embodiment P, further comprising a flow indicator control zone, wherein the flow indicator control zone is disposed in the porous carrier in the first fluid pathway, wherein the target cell-binding zone is disposed in the first fluid pathway between the sample-receiving zone and the flow indicator control zone.

Embodiment R is the device of any one of Embodiments L through Q, further comprising a removable first cover element that removably covers the first opening.

Embodiment S is the device of any one of Embodiments L through R, further comprising a removable second cover element that removably covers the second opening.

Embodiment T is the device of any one of Embodiments L through S, further comprising a removable third cover element that removably covers the sample port.

Embodiment U is the device of any one of Embodiments L through T, further comprising an absorbent body disposed proximate the second opening.

Embodiment V is the device of Embodiment U, as dependent on Embodiment S, wherein the absorbent body is coupled to the second cover element.

Embodiment W is the device of Embodiment T or Embodiment U, wherein the absorbent body is spaced apart from the porous carrier.

Embodiment X is the device of any one of the preceding Embodiments, the device further comprising a detachment member dimensioned to traverse the second fluid pathway from the first opening to the second opening, wherein a portion of the detachment member is slideably engaged in the second fluid pathway.

Embodiment Y is the device of Embodiment X, wherein the detachment member comprises a cutting structure.

Embodiment Z is the device of Embodiment X or Embodiment Y, wherein the detachment member is configured to urge an aqueous liquid through the second conduit.

Embodiment AA is a kit comprising the device of any one of Embodiments L through W.

Embodiment AB is the kit of Embodiment AA, further comprising a detachment member dimensioned to traverse the second fluid pathway from the first opening to the second opening.

Embodiment AC is the kit of Embodiment AB, wherein the detachment member comprises a cutting structure.

Embodiment AD is the kit of Embodiments AB or Embodiment AC, wherein the detachment member is configured to urge an aqueous liquid through the casing.

Embodiment AE is the kit of any one of Embodiments AA through AD, further comprising a wash liquid.

Embodiment AF is the kit of any one of Embodiments AA through AE, further comprising a release solution.

Embodiment AG is the kit of any one of Embodiments AA through AF, further comprising a reagent for nucleic acid amplification.

EXAMPLES

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is distilled water, and all molecular weights are weight average molecular weight.

Reference Example 1. Detection of Nucleic Acid from Microorganisms Captured in a Lateral-Flow Porous Support Rapid *Salmonella* Lateral Flow dipsticks (Part No. 3000034) were obtained from Romer Labs (Union, Mo.). A strain of *Salmonella* was grown overnight in Buffered Peptone Water and was diluted (i.e., serial 10-fold dilutions) in Butterfields Buffer. One milliliter of the $10^{-7}$ dilution was used to inoculate a PETRIFILM™ Enterobacteriaceae Count Plate (3M Company, St. Paul, Minn.). The plate was incubated according to the manufacturer's instructions and was found to contain 110 colony-forming units.

One of the dipsticks was placed into each of the $10^{-3}$, $10^{-4}$, $10^{-5}$, $10^{-6}$, and $10^{-7}$ serial dilutions of the *Salmonella* culture and the dipsticks were processed according to the manufacturer's instructions. The "control" line and the "target" line (which binds *Salmonella* microorganisms) from each dipstick were excised with a razor blade. Fresh gloves and razor blades were used to excise each line in order to avoid cross-contamination. Each excised line was resuspended in 100 µL of SS2 buffer (KCl, 3.19 g/L; (NH4)2SO4, 1.41 g/L; Tris base, 2.72 g/L; ProClin® 950, 0.526 g/L; polyvinylpyrolidone 0.43 g/L, Triton™ X-100, 80 g/L) in a 1.5-mL microcentrifuge tube. The tubes were placed in a heat block at 100° C. for 10 minutes to lyse any cells bound to the line. After boiling, the sample was mixed (using a micropipet) and 20 µL aliquots were withdrawn and used to reconstitute separate *Salmonella* reagent tablets (part number MDAS96NA, available from 3M Company, St. Paul, Minn.) of the 3M Molecular Detection System.

For comparison, 20 µL aliquots of the $10^{-3}$, $10^{-4}$, $10^{-5}$, $10^{-6}$, and $10^{-7}$ serial dilutions of the *Salmonella* culture were used to reconstitute separate *Salmonella* reagent tablets of the 3M Molecular Detection System. All of the reconstituted assays were processed in a 3M Molecular Detection System instrument (available from 3M Company, St. Paul, Minn.) according to the manufacturer's instructions. The presence or absence of detectable *Salmonella* in each assay is shown in Table 1.

TABLE 1

Detection of *Salmonella* bound to lateral flow dipsticks. A "+" sign denotes positive detection of *Salmonella* microorganisms in the sample. A "−" sign denotes no detection of *Salmonella* microorganism in the sample.

| Dilution | Portions excised from Lateral-flow Dipsticks | | Comparison (liquid suspensions) |
|---|---|---|---|
| | "Control" Line | "Target" Line | |
| $10^{-3}$ | + | + | + |
| $10^{-4}$ | + | + | + |
| $10^{-5}$ | + | + | + |
| $10^{-6}$ | + | + | − |
| $10^{-7}$ | − | − | − |

The results indicate the method of concentrating a target microorganism in a target cell-binding zone of a lateral flow device provided at least about a 10-fold enhancement in the detection of the target microorganism.

Example 1. Construction of a Lateral-Flow Sample Preparation Device

A device similar to the one shown in FIG. 11A was constructed with the exception that a layer of 3M double-sided tape was inserted between the first piece of the casing and the spacer element. Holes were cut into the double-sided tape such that they could be aligned with the first and second conduits to allow passage of liquid from the first and second conduits to the porous carrier. The spacer element was a strip of PET film (0.254 mm thick) with an opening large enough to encompass the porous carrier.

The first piece of the casing was constructed using PET film (0.254 mm thick). Two holes were bored through the first piece. The opening of an inverted microcentrifuge tube was adhered (using 3M™ Adhesive Transfer Tape 6035PC available from 3M Company, St. Paul, Minn.) to one of the holes to form the first conduit. The bottom of the tube had been cut off to convert the tube into a hollow cylinder. The barrel of a 1-milliliter disposable plastic syringe was adhered (using 3M™ Adhesive Transfer Tape 6035PC) to the other hole to form the second conduit. The plunger of the disposable syringe was used as the detachment member. The porous carrier was a strip (4 mm wide) of FUSION 5™ lateral flow material from Whatman. The second piece was a strip of PET film (0.254 mm thick) coated with an adhesive (3M™ Adhesive Transfer Tape 6035PC) that bonded the second piece to the spacer element. The second piece had a serrated hole that was aligned with the second conduit such that, when the detachment member was urged through the second conduit until the tip contacted the porous support, further pressure on the detachment member urged the porous carrier against the serrated edge, thereby cutting a portion of the porous carrier and expelling the portion through the serrated hole.

After assembling the device, the target cell-binding zone of each porous carrier was prepared. Two microliters of a suspension of two-micron BACTRACE™ anti-*E. coli* O157 latex agglutination beads (obtained from KPL, Gaithersburg, Md.) were added to 500 µL of deionized water, mixed, and added to the second conduits (i.e., the syringe barrels) of the device. The detachment member (i.e., the syringe plunger) was inserted into the conduit and depressed slowly, thereby urging the beads into the porous carrier. The plunger was withdrawn from the device and the device was dried under vacuum at 40° C. for two hours. This immobilized the beads in the porous matrix.

Example 2. Use of a Lateral-Flow Sample Preparation Device in a Method of Preparing a Sample and Detecting a Microorganism in Said Prepared Sample Sample preparation devices were prepared according to Example 1. Bacterial suspensions were prepared by suspending the bacteria a colony of *E. coli* O157 (picked from a blood agar plate) in Butterfield's buffer and serially-diluting (10-fold dilutions) the initial suspension in Butterfield's buffer. Six 20-microliter aliquots of each of the $10^{-2}$ dilution through the $10^{-6}$ dilution were analyzed for the presence of *E. coli* O157 using the 3M Molecular Detection System according to the manufacturer's instructions. The results, shown in Table 2, showed reproducible detection of *E. coli* O157 in aliquots taken from the $10^{-2}$ through $10^{-5}$ dilutions of the bacterial suspension. The results also showed a reproducible lack of detection of *E. coli* O157 in aliquots taken from the $10^{-6}$ dilution of the bacterial suspension

TABLE 2

Detection of the presence of E. coli O157 in serial dilutions of a bacterial suspension. The numerator shows the number of samples in which E. coli O157 was positively detected for each dilution. The denominator shows the number of samples tested for each dilution.

| Dilution | Test results (# positives/# samples) |
|---|---|
| $10^{-2}$ | 6/6 |
| $10^{-3}$ | 6/6 |
| $10^{-4}$ | 6/6 |
| $10^{-5}$ | 6/6 |
| $10^{-6}$ | 0/6 |

Two hundred fifty microliter aliquots of the $10^{-5}$, $10^{-6}$, and $10^{-7}$ serial dilutions were loaded into the first conduit of individual sample processing devices that were configured to detect E. coli O157 and the sample liquid was allowed to flow through the porous carrier for 10 minutes. After the 10 minutes, the detachment member (i.e., plunger) was used to eject the target cell-binding portion of the porous carrier from each device. Each target cell-binding portion was ejected into a separate reaction tube. One hundred microliters of SS2 solution was added to each reaction tube and the tubes were placed in a heat block at 100° C. for 10 minutes to lyse any cells bound to the target cell-binding portion. After cooling the tubes, 20 µL was removed from the reaction tube and was used to reconstitute E. coli O157 reagent tablets of the 3M Molecular Detection System. All of the reconstituted solutions were processed in a 3M Molecular Detection System instrument according to the manufacturer's instructions. The presence or absence of detectable E. coli O157 in each assay is shown in Table 3.

TABLE 3

Detection of the presence of E. coli O157 in the target cell-binding portions ejected from the sample processing devices tested in Example 2. A "+" sign denotes positive detection of E. coli microorganisms in the sample. A "−" sign denotes no detection of E. coli microorganisms in the sample.

| Dilution Tested | Results |
|---|---|
| $10^{-5}$ | + |
| $10^{-6}$ | + |
| $10^{-7}$ | − |

Comparison of the results shown in Table 2 with the results shown in Table 3 indicates the method of detecting microorganisms using the sample-processing device of the present disclosure is more sensitive than a conventional method of detection.

Example 3. Use of a Lateral-Flow Sample Preparation Device in a Method of Preparing a Sample that Includes a Wash Step in the Lateral Flow Device Sample preparation devices were prepared as described in Example 1. One device was prepared with anti-E. coli O157 latex agglutination beads (obtained from KPL) in the target cell-binding zone and the other was prepared with anti-E. coli O26 latex agglutination beads (obtained from KPL) in the target cell-binding zone. Axenic suspensions of E. coli O157 and E. coli O26, respectively, were prepared and diluted as described in Example 2. 250 microliter aliquots of the $10^{-5}$ dilution of each bacterial suspension were loaded into the sample-processing device configured to detect the corresponding bacteria and the samples were allowed to permeate through the porous carrier for 10 minutes. After 10 minutes, 500 µL of a wash solvent (Butterfield's buffer) was pipetted into the second conduit and was subsequently urged through the target cell-binding zone of the porous carrier using the detachment member (i.e., plunger). After the wash solvent was passed through the porous member, the detachment member was urged against the porous member until a portion (the target cell-binding zone) of the porous member was ejected from the device into a reaction tube. One hundred microliters of SS2 solution was added to each reaction tube and the tubes were placed in a heat block at 100° C. for 10 minutes to lyse any cells bound to the target cell-binding portion. After cooling the tubes, 20 µL was removed from the reaction tube and was used to reconstitute a corresponding reagent tablet (i.e., an E. coli O157 reagent tablet or an E. coli O26 reagent tablet) of the 3M Molecular Detection System. All of the reconstituted solutions were processed in a 3M Molecular Detection System instrument according to the manufacturer's instructions. The presence or absence of detectable E. coli in each assay is shown in Table 4.

TABLE 4

Detection of the presence of E. coli in the target cell-binding portions ejected from the sample processing devices tested in Example 3. A "+" sign denotes positive detection of E. coli microorganisms in the sample. A "−" sign denotes no detection of E. coli microorganisms in the sample.

| | Detection Beads | |
|---|---|---|
| Dilution Tested | E. coli O157 | E. coli O26 |
| $10^{-5}$ | + | − |

The results indicate that, even after washing the target cell-binding region in situ in the sample-processing device, the device was able to detect E. coli O157 microorganisms bound to the target cell-binding region.

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention claimed is:

1. A method of detecting a target microorganism, comprising:
    contacting a liquid sample with a porous carrier of a sample preparation device, the device comprising:
        a casing comprising a first and second opening; and
        the porous carrier;
            wherein the porous carrier comprises a sample-receiving zone at a first predefined location and a target cell-binding zone at a second predefined location, the porous carrier defining a first fluid pathway extending from the sample-receiving zone through the target cell-binding zone;
            wherein at least portion of the porous carrier is disposed in the casing;
            wherein a second fluid pathway extends through the casing from the first opening to the second opening, the second fluid pathway intersecting the porous carrier at the target cell-binding zone;
    allowing at least a portion of the liquid sample to move longitudinally through the porous carrier from the sample-receiving zone toward the target cell-binding zone;
    after the at least a portion of the liquid has moved to the target cell-binding zone, urging a detachment member that is slidably engaged with the second fluid pathway through the second fluid pathway from the first opening to the second opening and thereby expelling a portion of the target cell-binding zone; and
    processing the portion of the target cell-binding zone, or a cell released therefrom, to detect an indication of the target microorganism.

2. The method of claim 1, wherein the device further comprises a first cover element that covers the first opening or a second cover element that covers the second opening, wherein urging a detachment member through the second fluid pathway comprises urging the detachment member through the first cover element or the second cover element.

3. The method of claim 1, wherein the carrier is supported by a substrate, wherein urging a detachment member through the second fluid pathway to detach at least a portion of the target cell-binding zone further comprises using the detachment member to detach a portion of the substrate.

4. The method of claim 1, wherein, after the at least a portion of the liquid has moved to the target cell-binding zone, the method further comprises a step of passing a wash solvent through the porous carrier via the second fluid pathway.

5. The method of claim 1, further comprising positioning a receptacle proximate the second opening, wherein expelling a portion of the target cell-binding zone or expelling the part of the release solution further comprises moving the portion of the target cell-binding zone or moving the part of the release solution into the receptacle.

6. The method of claim 1, wherein processing the portion of the analyte-binding zone or processing the part of the release solution to detect an indication of the target microorganism further comprises processing the portion of the analyte-binding zone or processing the part of the release solution to detect a biomolecule associated with the target microorganism.

7. The method of claim 1, wherein processing the portion of the target cell-binding zone or processing the part of the release solution comprises amplifying a nucleic acid sequence, wherein the nucleic acid sequence comprises a nucleotide sequence associated with the target microorganism.

8. A device, comprising:
    a casing comprising an interior, a first opening, and a second opening;
    a porous carrier comprising a sample-receiving zone and a target cell-binding zone; and
    a detachment member dimensioned to traverse a second fluid pathway from the first opening to the second opening, wherein a portion of the detachment member is slideably engaged in the second fluid pathway;
    wherein the porous carrier defines a first fluid pathway that extends from the sample-receiving zone to the target cell-binding zone;
    wherein at least portion of the porous carrier is disposed in the interior of the casing;
    wherein a second fluid pathway comprising a central axis extends through the casing from the first opening and the second opening, the second fluid pathway intersecting the porous carrier at the target cell-binding zone;
    wherein the central axis is oriented orthogonal to the porous carrier.

9. The device of claim 8, further comprising a sample port that provides access to the sample-receiving zone, wherein the sample-receiving zone is disposed in the interior of the casing.

10. The device of claim 8, wherein the casing further comprises a first conduit that extends from the sample port to the interior of the casing.

11. The device of claim 8, wherein the casing further comprises a second conduit that extends from the first opening to the interior of the casing.

12. The device of claim 8, further comprising a flow indicator disposed in the porous carrier in the first fluid pathway.

13. The device of claim 8, further comprising an absorbent body disposed proximate the second opening.

14. The device of claim 8, wherein the detachment member comprises a cutting structure.

15. A kit comprising the device of claim 8, and a reagent for nucleic acid amplification.

16. The kit of claim 15, further comprising a detachment member dimensioned to traverse the second fluid pathway from the first opening to the second opening.

17. The kit of claim 16, wherein the detachment member comprises a cutting structure.

* * * * *